(12) United States Patent
Nakazawa et al.

(10) Patent No.: US 11,089,965 B2
(45) Date of Patent: Aug. 17, 2021

(54) BLOOD PRESSURE INFORMATION CALCULATING DEVICE, BLOOD PRESSURE INFORMATION CALCULATING METHOD, BLOOD PRESSURE INFORMATION CALCULATING PROGRAM, AND RECORDING MEDIUM FOR RECORDING SAID PROGRAM

(71) Applicant: HAMAMATSU PHOTONICS K.K., Hamamatsu (JP)

(72) Inventors: Tomoya Nakazawa, Hamamatsu (JP); Rui Sekine, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 526 days.

(21) Appl. No.: 15/778,745

(22) PCT Filed: Mar. 30, 2016

(86) PCT No.: PCT/JP2016/060512
§ 371 (c)(1),
(2) Date: May 24, 2018

(87) PCT Pub. No.: WO2017/090259
PCT Pub. Date: Jun. 1, 2017

(65) Prior Publication Data
US 2018/0353088 A1    Dec. 13, 2018

(30) Foreign Application Priority Data

Nov. 27, 2015 (JP) .............................. JP2015-231628

(51) Int. Cl.
*A61B 5/021* (2006.01)
*A61B 5/022* (2006.01)
*A61B 5/00* (2006.01)

(52) U.S. Cl.
CPC ........ *A61B 5/02108* (2013.01); *A61B 5/0075* (2013.01); *A61B 5/022* (2013.01);
(Continued)

(58) Field of Classification Search
CPC ............. A61B 5/02108; A61B 5/0075; A61B 5/7207; A61B 5/7257; A61B 5/022; A61B 5/6814; A61B 5/6826
(Continued)

(56) References Cited

U.S. PATENT DOCUMENTS

| 6,036,651 A | 3/2000 | Inukai et al. | |
|---|---|---|---|
| 2008/0039731 A1* | 2/2008 | McCombie | ........ A61B 5/02255 600/485 |
| 2009/0209868 A1* | 8/2009 | Hersh | ................ A61B 5/02225 600/485 |

FOREIGN PATENT DOCUMENTS

| CN | 1158077 A | 8/1997 |
|---|---|---|
| CN | 1535653 A | 10/2004 |

(Continued)

OTHER PUBLICATIONS

International Preliminary Report on Patentability dated Jun. 7, 2018 for PCT/JP2016/060512.

*Primary Examiner* — Jacqueline Cheng
*Assistant Examiner* — Tho Q Tran
(74) *Attorney, Agent, or Firm* — Faegre Drinker Biddle & Reath LLP

(57) ABSTRACT

A blood pressure information calculating device includes an input unit to which a waveform based on a pulse wave of the subject and reference blood pressure information serving as a reference for calculating the blood pressure information on the basis of the waveform based on the pulse wave are input, a conversion unit that calculates a phase spectrum of a waveform based on the pulse wave by performing Fourier transformation on the waveform based on the pulse wave, a
(Continued)

calculation unit that calculates a correction value using at least one of a phase of a main wave corresponding to a pulse of the subject and a phase of a second harmonic wave of the main wave on the basis of the phase spectrum, and a calculation unit that calculates an average blood pressure by correcting the reference blood pressure information using the correction value.

16 Claims, 15 Drawing Sheets

(52) U.S. Cl.
CPC .......... *A61B 5/7207* (2013.01); *A61B 5/7257* (2013.01); *A61B 5/6814* (2013.01); *A61B 5/6826* (2013.01)

(58) Field of Classification Search
USPC ........................................................ 600/481
See application file for complete search history.

(56) References Cited

FOREIGN PATENT DOCUMENTS

| | | |
|---|---|---|
| CN | 102955889 A | 3/2013 |
| CN | 103479343 A | 1/2014 |
| CN | 1251027 | 2/2018 |
| JP | H05-7558 A | 1/1993 |
| JP | WO-99/26529 A1 | 6/1999 |
| JP | H11-318838 A | 11/1999 |
| JP | WO-01/78599 A2 | 10/2001 |
| JP | 2002-325739 A | 11/2002 |
| JP | 2003-000555 A | 1/2003 |
| JP | 2003-530191 A | 10/2003 |
| JP | 2006-346164 A | 12/2006 |
| JP | 2008-295517 A | 12/2008 |
| JP | 4759860 B2 | 8/2011 |

\* cited by examiner

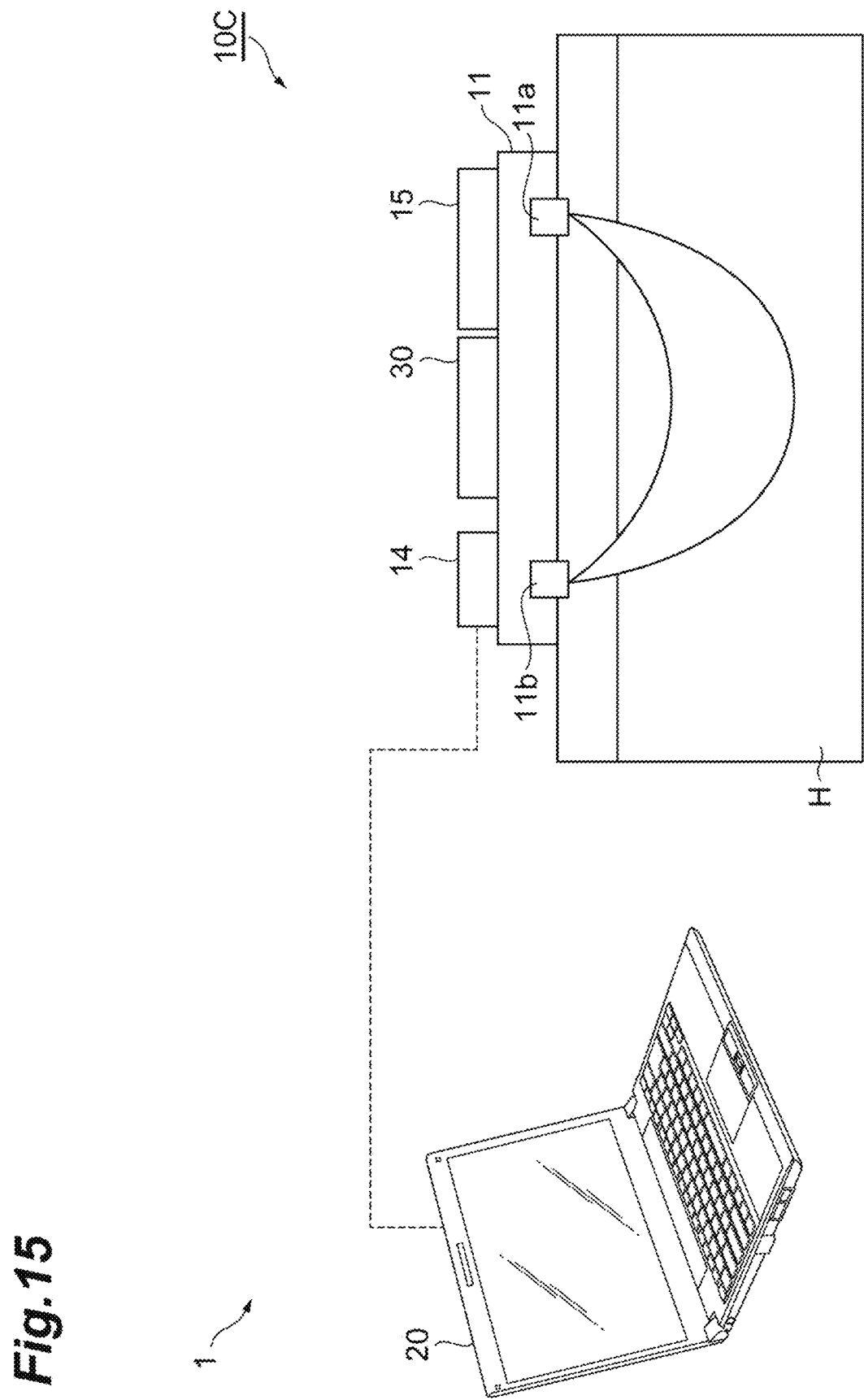

BLOOD PRESSURE INFORMATION CALCULATING DEVICE, BLOOD PRESSURE INFORMATION CALCULATING METHOD, BLOOD PRESSURE INFORMATION CALCULATING PROGRAM, AND RECORDING MEDIUM FOR RECORDING SAID PROGRAM

TECHNICAL FIELD

The present invention relates to a blood pressure information calculating device, a blood pressure information calculating method, a blood pressure information calculating program, and a recording medium for recording the program.

BACKGROUND ART

In the related art, a method of obtaining a blood pressure value by analyzing a pulse wave is known as a noninvasive blood pressure measurement method in which a burden on a subject is reduced. For example, a detection device described in Patent Literature 1 detects a pulse wave (a volume pulse wave) by detecting variation in the amount of reflected light or the amount of transmitted light according to irradiation of an artery with light and calculates a blood pressure waveform using a transfer function stored in advance and a pulse waveform. That is, the blood pressure waveform is calculated by performing Fourier transformation on the pulse waveform, dividing a resultant waveform by the transfer function, and performing inverse Fourier transformation on a result of the division.

CITATION LIST

Patent Literature

[Patent Literature 1] Japanese Patent No. 4759860

SUMMARY OF INVENTION

Technical Problem

A transfer function calculated in advance using a blood pressure waveform measured by a sphygmomanometer in advance and a pulse waveform detected in advance is stored in the detection device of the related art described above. Therefore, when a blood pressure waveform is repeatedly calculated, the same transfer function tends to be used repeatedly several times. Therefore, in the related art, the accuracy of calculation of a value regarding the blood pressure waveform may become degraded with time.

The present invention relates to a blood pressure information calculating device, a blood pressure information calculating method, a blood pressure information calculating program, and a recording medium on which the program is stored, in which the accuracy of calculation of a value regarding a blood pressure waveform can be maintained without requiring a complicated operation.

Solution to Problem

The inventors of the present invention have found that there is a correlation between a spectral component of a waveform based on a pulse wave and blood pressure information as a result of performing extensive research on a method of obtaining blood pressure information such as an average blood pressure regarding the blood pressure waveform. Further, the inventors of the present invention have revealed a relationship between the spectral component and the blood pressure information, and have conceived that blood pressure information can be derived from the waveform based on the pulse wave. Then, they have completed the present invention.

That is, an aspect of the present invention is a blood pressure information calculating device for calculating blood pressure information regarding a blood pressure value of an inspection target, and includes an input unit for inputting a waveform based on a pulse wave of the inspection target and reference blood pressure information serving as a reference for calculating the blood pressure information on the basis of the waveform based on the pulse wave; a spectrum calculation unit for calculating a phase spectrum of a waveform based on the pulse wave by performing Fourier transformation on the waveform based on the pulse wave; a correction value calculation unit for calculating a correction value using at least one of a phase of a main wave which is a frequency corresponding to a pulse of the inspection target and a phase of a second harmonic wave corresponding to a second harmonic wave of the main wave on the basis of the phase spectrum; and a blood pressure information calculation unit for calculating the blood pressure information by correcting the reference blood pressure information using the correction value.

Further, another aspect of the present invention is a blood pressure information calculating method of calculating blood pressure information regarding a blood pressure value of an inspection target, and includes an acquisition step of acquiring a waveform based on a pulse wave of the inspection target and reference blood pressure information serving as a reference for calculating the blood pressure information on the basis of the waveform based on the pulse wave; a spectrum calculation step of calculating a phase spectrum of a waveform based on the pulse wave by performing Fourier transformation on the waveform based on the pulse wave; a correction value calculation step of calculating a correction value using at least one of a phase of a main wave which is a frequency corresponding to a pulse of the inspection target and a phase of a second harmonic wave corresponding to a second harmonic wave of the main wave on the basis of the phase spectrum; and a blood pressure information calculation step of calculating the blood pressure information by correcting the reference blood pressure information using the correction value.

Further, another aspect of the present invention is a blood pressure information calculating program for causing a computer to execute a process of calculating blood pressure information regarding a blood pressure value of an inspection target, the program causing the computer to function as: an input unit for inputting a waveform based on a pulse wave of the inspection target and reference blood pressure information serving as a reference for calculating the blood pressure information on the basis of the waveform based on the pulse wave; a spectrum calculation unit for calculating a phase spectrum of a waveform based on the pulse wave by performing Fourier transformation on the waveform based on the pulse wave; a correction value calculation unit for calculating a correction value using at least one of a phase of a main wave which is a frequency corresponding to a pulse of the inspection target and a phase of a second harmonic wave corresponding to a second harmonic wave of the main wave on the basis of the phase spectrum; and a blood pressure information calculation unit for calculating the blood pressure information by correcting the reference blood pressure information using the correction value.

According to the blood pressure information calculating device, the blood pressure information calculating method, the blood pressure information calculating program, or the recording medium for recording the program according to the above aspect of the present invention, the correction value is calculated using at least one of a phase of the main wave that is a frequency corresponding to the pulse and a phase of the second harmonic wave corresponding to a second harmonic wave of the main wave on the basis of the phase spectrum calculated by performing Fourier transformation on the waveform based on the pulse, and blood pressure information is calculated by correcting the reference blood pressure information using the correction value. Since the phase of the main wave or the phase of the second harmonic wave calculated in this way is highly correlated with the blood pressure information, the blood pressure information obtained by correcting the reference blood pressure information using the correction value calculated from the phase has high accuracy. Therefore, it is possible to maintain the accuracy of the calculation of the value regarding a blood pressure waveform without repeating complicated operations, such as a measurement operation using the sphygmomanometer or calculation of a resultant blood pressure waveform.

Advantageous Effects of Invention

According to an aspect of the present invention, it is possible to maintain accuracy of calculation of a value regarding a blood pressure waveform without a complicated operation being required.

BRIEF DESCRIPTION OF DRAWINGS

FIG. 15 is a schematic configuration diagram illustrating a blood pressure information calculating device according to the modification example.

DESCRIPTION OF EMBODIMENTS

Figure 1:
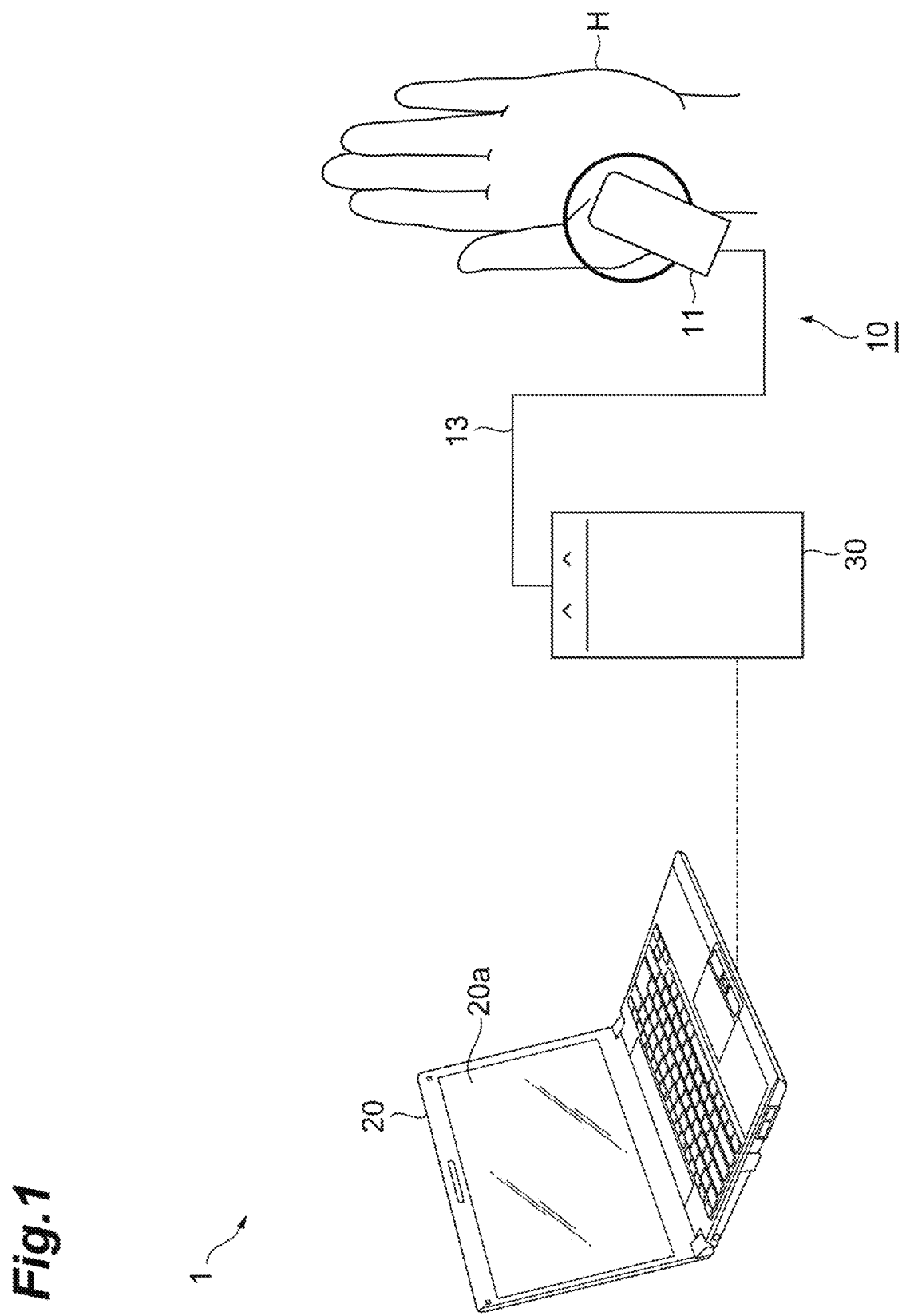
FIG. 1 is a schematic configuration diagram illustrating a blood pressure information calculation system including a blood pressure information calculating device according to a first embodiment of the present invention.

Hereinafter, embodiments of the present invention will be described in detail with reference to the accompanying drawings. In the description, the same elements or elements having the same functions are denoted with the same reference numerals, and duplicated description thereof will be omitted.

First Embodiment

First, an overview of a blood pressure information calculation system including a blood pressure information calculating device according to a first embodiment of the present invention will be described. The blood pressure information calculation system according to the embodiment is a system that calculates blood pressure information from a relative blood pressure waveform that is a waveform based on a pulse wave of an inspection target (subject). The relative blood pressure waveform is information corresponding to temporal change in the relative blood pressure of the subject. The relative blood pressure waveform can be acquired by, for example, a near infra-red spectroscopy (NIRS) device, a pulse oximeter, or a tonometer. For example, in an NIRS device, by irradiating a living body with light and detecting an intensity of reflected light of the living body, a change in blood volume over time occurring at a predetermined position in the living body is measured from a surface of the living body, and a result thereof is acquired as a blood pressure waveform. In the pulse oximeter, an oxygen saturation of arterial blood is measured, and a result thereof is acquired as a relative blood pressure waveform. In the tonometer, a relative change in arterial pressure is measured by a blood pressure sensor attached to a radial artery or the like using a blood vessel wall motion due to blood pressure variation, and a result thereof is acquired as the relative blood pressure waveform. Further, the relative blood pressure waveform may be acquired by, for example, plethysmography, an electromagnetic blood flow meter, an ultrasonic blood flow meter, or a laser blood flow meter. In the embodiment, a case in which a volume pulse wave acquired by an NIRS device is used as the relative blood pressure waveform will be described.

The relative blood pressure waveform has a correspondence relationship with a blood pressure waveform in which temporal change in an absolute value of blood pressure in a blood vessel is taken as a waveform (hereinafter also referred to as an "absolute blood pressure waveform"), and has a value different from that of the absolute blood pressure waveform but has a shape similar to that of the absolute blood pressure waveform. The blood pressure information calculation system calculates and outputs blood pressure information of the subject on the basis of the relative blood pressure waveform. The blood pressure information is information on a blood pressure value of a subject, and includes, for example, a maximum blood pressure which is a systolic blood pressure value that is highest in a systole, a minimum blood pressure which is a diastolic blood pressure that is lowest in a diastole, and an average blood pressure value which is a temporal average value of a blood pressure value.

Figure 2:
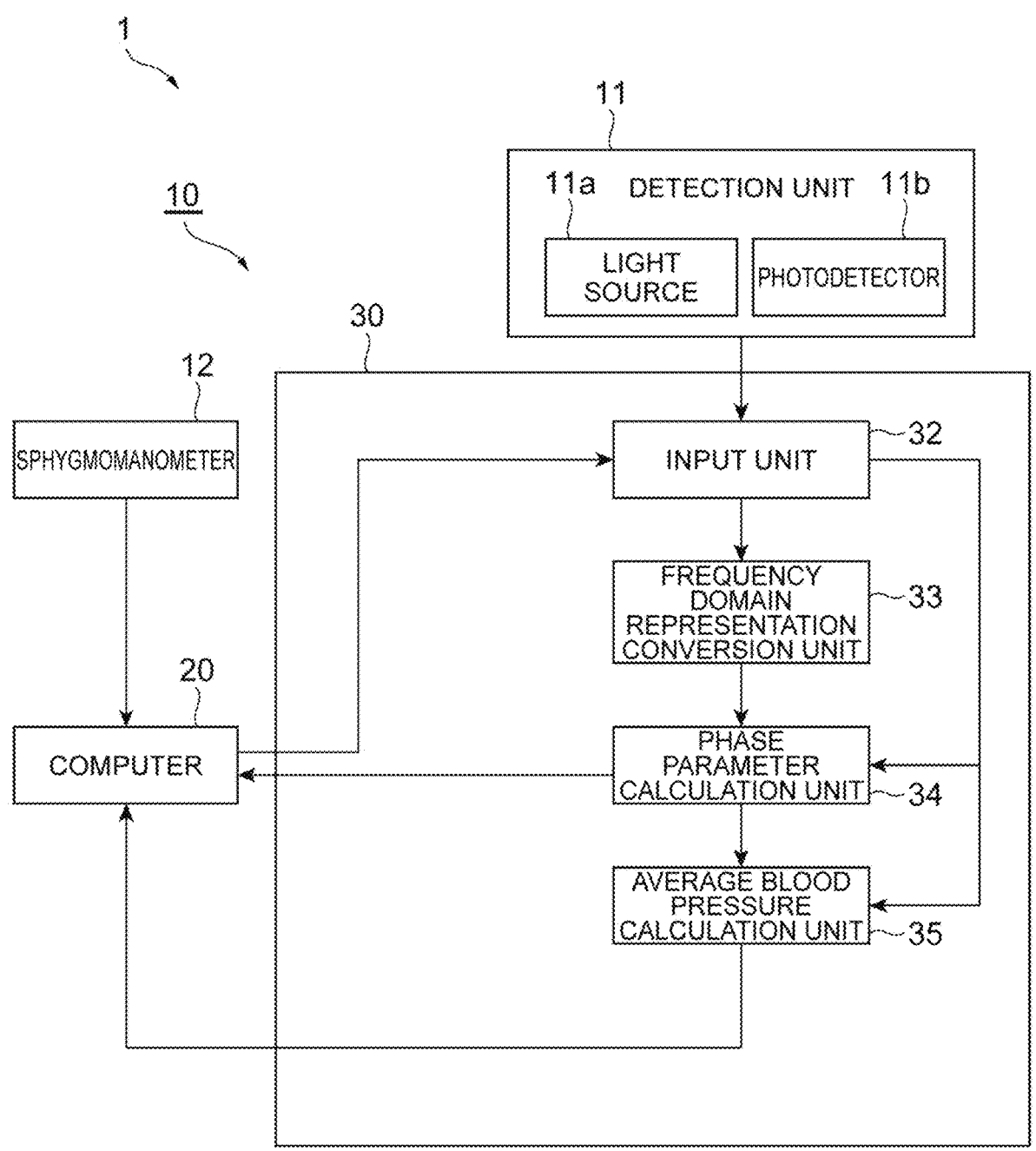
FIG. 2 is a functional block diagram of a processing unit in FIG. 1.

FIG. 1 is a schematic configuration diagram illustrating a blood pressure information calculation system including a blood pressure information calculating device according to a first embodiment of the present invention. FIG. 2 is a functional block diagram of a processing unit in FIG. 1. As illustrated in FIG. 1, the blood pressure information calculation system 1 includes a blood pressure information calculating device 10 and a computer 20.

The blood pressure information calculating device 10 acquires a volume pulse wave (a relative volume wave) as a relative blood pressure waveform in a living body serving as a subject using, for example, near infrared spectroscopy (NIRS). In addition, the blood pressure information calculating device 10 calculates the blood pressure information on the subject on the basis of the acquired relative blood pressure waveform. In the embodiment, the blood pressure information calculating device 10 calculates the average blood pressure as the blood pressure information. A portable near infrared tissue oxygen monitor device, for example, is used as the blood pressure information calculating device 10. The blood pressure information calculating device 10 includes a detection unit 11 (an acquisition unit) and a processing unit 30.

The detection unit 11 detects a signal for acquiring the relative blood pressure waveform. The detection unit 11 has a probe shape that comes into contact with a surface (a palm of a hand in this embodiment) of a living body H that is the subject. The detection unit 11 includes a light source 11a and a photodetector 11b (see FIG. 2), and radiates near-infrared light from the light source 11a from the surface of the living body H toward the inside thereof, and detects light from the inside of the living body H generated due to the irradiation of the near-infrared light from the light source 11a using the photodetector 11b. Accordingly, the detection unit 11 acquires an absorbance when the light passes through the inside of the living body H. Since this absorbance changes according to the blood volume at a position with which the detection unit 11 comes in contact in the living body H, temporal change in the absorbance corresponds to a volume pulse wave. Examples of components that absorb the light in the blood include erythrocytes, hemoglobin contained in the erythrocytes, and moisture. The detection unit 11 detects the volume pulse wave on the basis of a detection signal from the photodetector 11b and acquires the volume pulse wave as the relative blood pressure waveform. For example, a detection rate of the detection unit 11 is about 1 kHz, and the detection unit 11 can detect a variation at a frequency equal to or higher than 22 Hz which is a frequency about six times a maximum heart rate. The detection unit 11 is electrically connected to the processing unit 30 via a cable 13, and transmits the acquired relative blood pressure waveform to the processing unit 30 via the cable 13. That is, the detection unit 11 is an acquisition unit that acquires the relative blood pressure waveform and inputs the relative blood pressure waveform to the processing unit 30.

The processing unit 30 receives the relative blood pressure waveform from the detection unit 11. The processing unit 30 calculates the average blood pressure by performing a predetermined process on the basis of the input relative blood pressure waveform. Details of the predetermined process will be described below. It is known that the volume pulse wave may be influenced by viscoelastic characteristics of the blood vessel. The viscoelastic characteristics of the blood vessel are characteristics of a behavior of viscoelasticity of the blood vessel being exhibited, that is, both elasticity and viscosity in the blood vessel. Therefore, when the input volume pulse wave is strongly influenced by the viscoelastic characteristics, a relative blood pressure waveform on which this influence has been reduced by correcting the volume pulse wave using a viscoelastic characteristics correction value indicating the viscoelastic characteristics of the blood vessel may be acquired, and the average blood pressure may be calculated by performing a predetermined process on the basis of the relative blood pressure waveform. Further, the processing unit 30 transmits the blood pressure information including the calculated average blood pressure to the computer 20 through wireless communication or the like.

The computer 20 has the reference blood pressure information on the subject measured by a cuff type sphygmomanometer, a catheter type sphygmomanometer, or the like stored therein in advance, and transmits the reference blood pressure information to the processing unit 30 through wireless communication or the like. Examples of the reference blood pressure information may include a maximum blood pressure and a minimum blood pressure or may include the average blood pressure itself. The reference blood pressure information is information serving as a reference for calculation of blood pressure information on the basis of the relative blood pressure waveform, and is input by a user in advance into the computer 20. In addition, the blood pressure information calculation system 1 may include a sphygmomanometer 12 (FIG. 2) that detects maximum and minimum blood pressures of a subject, such as a cuff type sphygmomanometer. In such a configuration, the computer 20 receives the reference blood pressure information based on a detection result of maximum and minimum blood pressures from the sphygmomanometer 12 through wireless communication, wired communication, or the like. The computer 20 has a display unit such as the display 20a and displays information including the blood pressure information received from the processing unit 30 on the display 20a. It should be noted that the computer 20 and the blood pressure information calculating device 10 may be electrically connected through a cable or the like. The computer 20 may receive information from the processing unit 30 through wired communication or may transmit information to the processing unit 30 through wired communication. Further, the sphygmomanometer 12 may be a catheter-type sphygmomanometer that detects the absolute blood pressure waveform of the subject, and the computer 20 may receive the reference blood pressure information based on a detection result of the absolute blood pressure waveform.

As illustrated in FIG. 2, the processing unit 30 includes an input unit 32, a frequency domain representation conversion unit (a spectrum calculation unit) 33, a phase parameter calculation unit (a correction value calculation unit) 34, and an average blood pressure calculation unit (a blood pressure information calculation unit) 35.

A relative blood pressure waveform p' is input from the detection unit 11 to the input unit 32. The input unit 32 outputs information on the input relative blood pressure waveform p' to the frequency domain representation conversion unit 33 and the phase parameter calculation unit 34. Further, the input unit 32 obtains an initial average blood pressure on the basis of the reference blood pressure information received from the computer 20, and outputs information on this initial average blood pressure to the average blood pressure calculation unit 35 as reference blood pressure information. Specifically, on the basis of a maximum blood pressure $p_{Max}$ and a minimum blood pressure $p_{Min}$ included in the reference blood pressure information, the input unit 32 calculates an initial average blood pressure $p_{0Ave}$ using Equation (1) below:

[Math. 1]
$$p_{0Ave} = p_{Min} + \frac{1}{3}(p_{Max} + p_{Min}) \quad (1)$$

and outputs the initial average blood pressure $p_{0Ave}$ to the average blood pressure calculation unit 35. In this case, the input unit 32 may acquire the information on the absolute blood pressure waveform p as the reference blood pressure information from the computer 20, and calculate the initial average blood pressure $p_{0Ave}$ according to Equation (2) below using the absolute blood pressure waveform p:

[Math. 2]
$$p_{0Ave} = \frac{1}{T}\int_0^T p\,dt. \quad (2)$$

The parameter T in Equation (2) indicates a period of one beat, the variable t indicates time, and the absolute blood pressure waveform p is a function of time t. Further, the input unit 32 may acquire the reference blood pressure information including the average blood pressure from the computer 20 and output the average blood pressure as the initial average blood pressure $p_{0Ave}$.

The frequency domain representation conversion unit 33 is a spectrum calculation unit that generates an intensity spectrum P(f) of the relative blood pressure waveform and a phase spectrum arg(P(f)) of the relative blood pressure waveform by performing Fourier transformation on the relative blood pressure waveform p' input by the input unit 32. Here, the variable f indicates a frequency. That is, the frequency domain representation conversion unit 33 converts the relative blood pressure waveform p', which is a function of the time indicated in a time domain representation, into the intensity spectrum P(f) of the relative blood pressure waveform and the phase spectrum arg(P(f)) of the relative blood pressure waveform, which are functions of the frequency indicated in a frequency domain representation. The frequency domain representation conversion unit 33 outputs information on the calculated intensity spectrum P(f) and the calculated phase spectrum arg(P(f)) to the phase parameter calculation unit 34. It should be noted that the frequency domain representation conversion unit 33 may calculate the intensity spectrum and the phase spectrum of the relative blood pressure waveform by performing the Fourier transformation on the relative blood pressure waveform p' obtained by reducing an influence of viscoelastic characteristics of the blood vessel by correcting the input volume pulse wave using the viscoelastic characteristics correction value indicating the viscoelastic characteristics of the blood vessel.

Using the information on the intensity spectrum P(f) and the phase spectrum arg(P(f)) calculated by the frequency domain representation conversion unit 33, the phase parameter calculation unit 34 corrects the initial average blood pressure $p_{0Ave}$ which is initial blood pressure information and calculates a phase parameter (correction value) θ for calculating the average blood pressure. That is, the phase parameter calculation unit 34 specifies a frequency at which a peak of the intensity spectrum P(f) becomes a maximum value, sets this frequency as a frequency $f_1$ of the main wave corresponding to the pulse of the subject, and sets a frequency $f_n = n \times f_1$ (n=2, 3, ...) that is an integer multiple of such a frequency as a frequency of an n-time wave (a n-th harmonic). Generally, a heart rate of a human being is 0.5 to 3.67 Hz, and in this frequency range, a frequency corresponding to the largest peak of the intensity spectrum is the heart rate. Using the set frequencies $f_1, f_2, f_3, \ldots$ of the main wave and an n-time wave, the phase parameter calculation unit 34 calculates the phase parameter θ using Equation (3) below:

[Math. 3]
$$\theta = \sum_{n=1}^{N} |P(f_n)| \arg(P(f_n)) \quad (3)$$

and outputs the phase parameter θ to the average blood pressure calculation unit 35. The parameter N in Equation (3) is a predetermined natural number. Specifically, the phase parameter calculation unit 34 calculates a sum of a product $P(f_1) \times \arg(P(f_1))$ of the intensity value of the intensity spectrum and the phase value of the phase spectrum at the frequency of the main wave and a product $P(f_n) \times \arg(P(f_n))$ of the intensity value of the intensity spectrum and the phase value of the phase spectrum at the frequency of the n-time wave (n=2, 3, ...) to obtain the phase parameter θ. Thus, the phase parameter θ is obtained as a value obtained by summing the weighted phase values from the main wave to the n-time wave.

Figure 3:
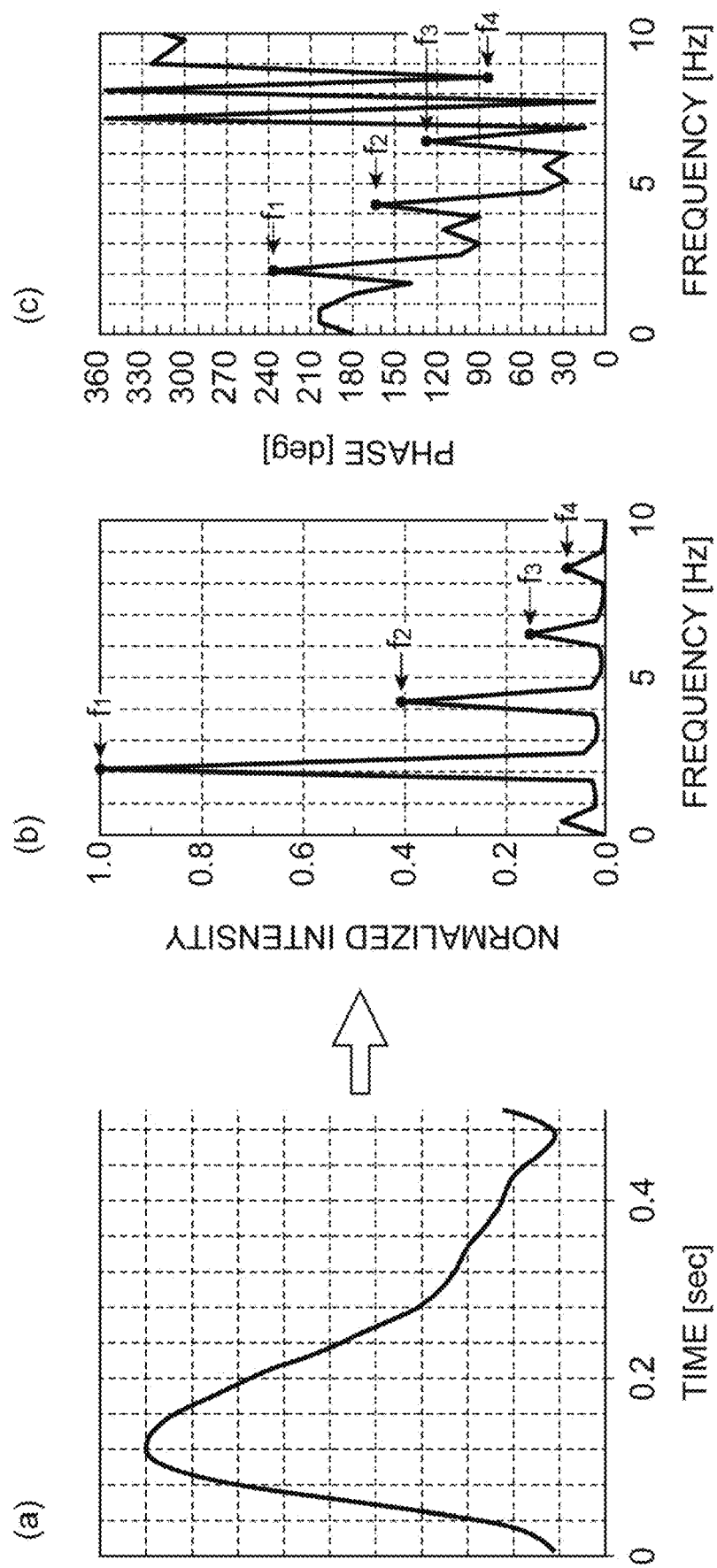
FIG. 3 is graphs illustrating an example of a relative blood pressure waveform input by an input unit 32 of FIG. 2, an example of an intensity spectrum of a relative blood pressure waveform calculated by a frequency domain representation conversion unit 33 of FIG. 2, and an example of a phase spectrum of the relative blood pressure waveform calculated by the frequency domain representation conversion unit 33 in FIG. 2.
Figure 4:
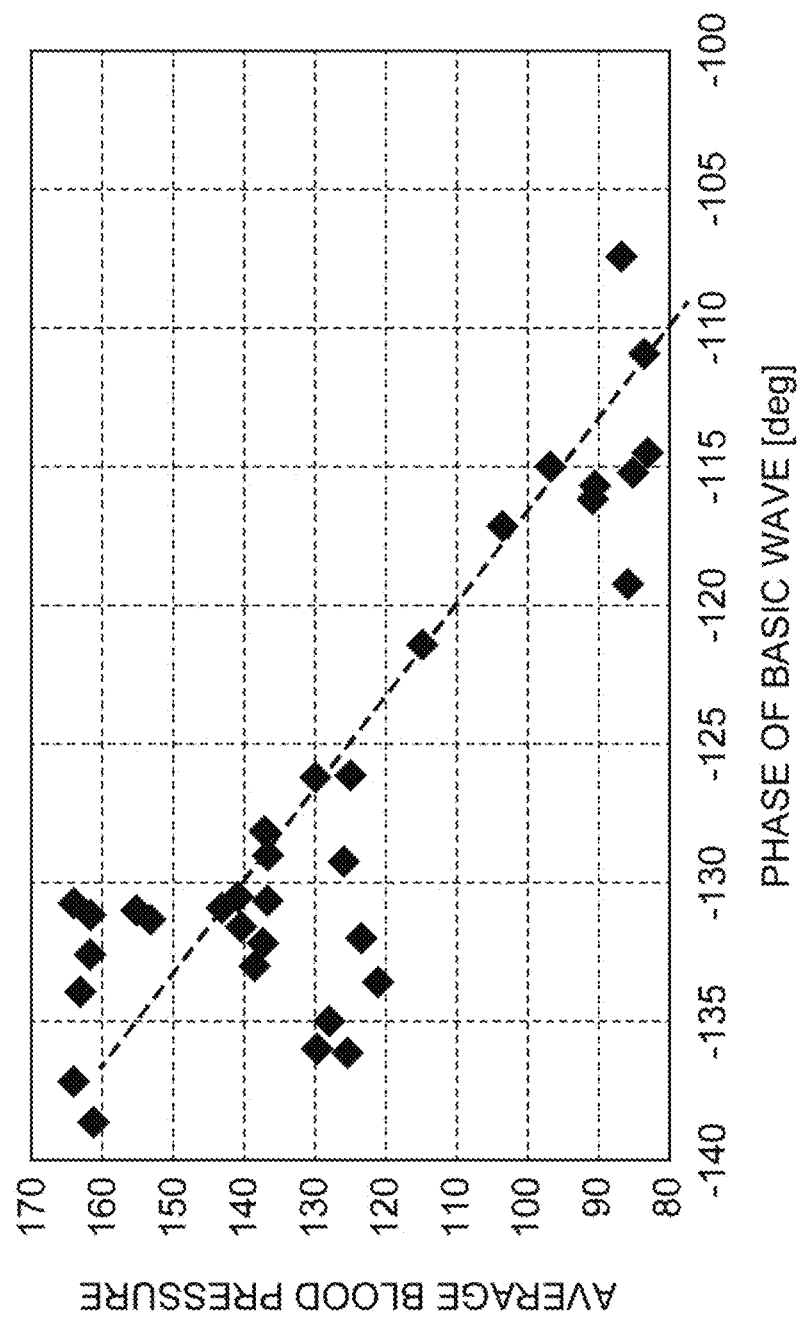
FIG. 4 is a graph illustrating a result of acquiring a relationship between a calculated value of a phase value of a main wave and an average blood pressure actually measured by a sphygmomanometer through a plurality of experiments.
Figure 5:
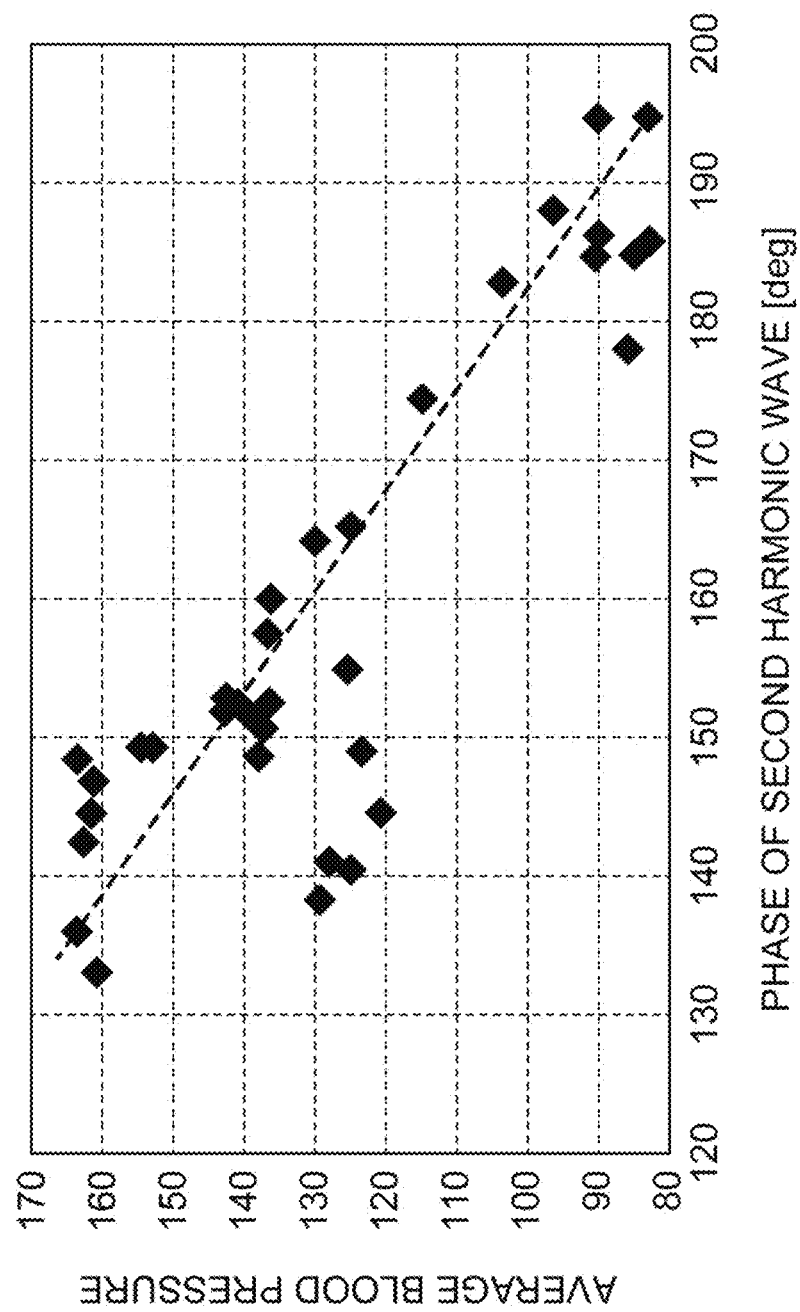
FIG. 5 is a graph illustrating a result of acquiring a relationship between a calculated value of a phase value of a second harmonic wave and the average blood pressure actually measured by the sphygmomanometer through a plurality of experiments.

FIG. 3 illustrates an example of the relative blood pressure waveform p' input by the input unit 32 in a part (a), illustrates an example of an intensity spectrum P(f) of the relative blood pressure waveform p' calculated by the frequency domain representation conversion unit 33 in a part (b), and illustrates an example of the phase spectrum arg(P(f)) of the relative blood pressure waveform p' calculated by the frequency domain representation conversion unit 33 in a part (c). As illustrated in FIG. 3, the frequency corresponding to the largest peak of the intensity spectrum P(f) of the relative blood pressure waveform p' and frequencies that are an integer multiple thereof are set as frequencies $f_1, f_2, f_3, \ldots$ of the main wave and the n-time wave. Using the value arg(P(f)) of the phase spectrum corresponding to these frequencies, the phase parameter θ is calculated. The phase parameter θ calculated in this way is highly correlated with the blood pressure information such as the average blood pressure at the time of measurement of the relative blood pressure waveform p' of the subject. FIG. 4 illustrates a result of acquiring a relationship between the calculated value of the phase value $arg(P(f_1))$ of the main wave and the average blood pressure actually measured by the sphygmomanometer through a plurality of experiments, and FIG. 5 illustrates a result of acquiring a relationship between the calculated value of the phase value $arg(P(f_2))$ of the second harmonic wave and the average blood pressure actually measured by the sphygmomanometer through a plurality of experiments. Thus, it has been found that there is a constant correlation between each of the phase values $arg(P(f_1))$ and $arg(P(f_2))$ of the main wave and the second harmonic wave and the average blood pressure.

It is preferable for the phase parameter calculation unit 34 to calculate the phase parameter θ using at least one of the phase value $arg(P(f_1))$ of the main wave and the phase value $arg(P(f_2))$ of the second harmonic wave in order to obtain a correction value highly correlated with the blood pressure information in consideration of the tendency of the above correlation. Further, it is preferable for the phase parameter calculation unit 34 to calculate the phase parameter θ using at least a value obtained by weighting any one of the phase values with one intensity value corresponding to a frequency at which the phase value has been obtained among the two intensity values $P(f_1)$ and $P(f_2)$. Further, it is preferable for the phase parameter calculation unit 34 to calculate the phase parameter θ by minimally using a sum of the phase values $P(f_1) \times arg(P(f_1))$ and $P(f2) \times arg(P(f_2))$ of the main wave and the second harmonic wave weighted with the intensity value. It is possible to obtain high-accuracy blood pressure information using such a phase parameter θ as the correction value. In the embodiment, the phase parameter calculation unit 34 calculates the phase parameter using a sum of the phase values $P(f_n) \times arg(P(f_n))$ (n=1 to 4) from the main wave to the fourth harmonic wave weighted by the intensity value. Specifically, according to the example illustrated in FIG. 3, the phase values $arg(P(f_n))$=236.30, 161.56, 128.32, 84.75 [deg] from the main wave to the fourth harmonic wave are obtained, and the intensity values $P(f_n)$=1.0, 0.41, 0.15, 0.08 [relative intensity] from the main wave to the fourth harmonic wave are obtained. In this case, by substituting these values into Equation (3) above, the phase parameter calculation unit 34 calculates the phase parameter θ as in the following equation:

θ=1.0×236.30+0.41×161.56+0.15×128.32+0.08× 84.75=327.93.

Here, the phase parameter calculation unit 34 may calculate the phase parameter using a sum of the phase values $P(f_n) \times arg(P(f_n))$ (n=1 to 5) weighted by the intensity value from the main wave to a from the fifth harmonic wave.

Further, the phase parameter calculation unit 34 acquires the initial phase parameter $\theta_0$ corresponding to the absolute blood pressure waveform of a detection source of the initial average blood pressure $p_{0Ave}$, as the reference blood pressure information. That is, the phase parameter calculation unit 34 acquires the initial phase parameter $\theta_0$ by executing Fourier transformation using the frequency domain representation conversion unit 33 and calculation using Equation (3) above with respect to the absolute blood pressure waveform p output from the input unit 32. Further, the phase parameter calculation unit 34 may acquire the initial phase parameter $\theta_0$ by executing Fourier transformation using the frequency domain representation conversion unit 33 and calculation using Equation (3) with respect to the relative blood pressure waveform p' obtained simultaneously with the detection of the initial average blood pressure $p_{Ave}$. In addition, the phase parameter calculation unit 34 may acquire the initial phase parameter $\theta_0$ included in the reference blood pressure information from the computer 20 via the input unit 32.

The average blood pressure calculation unit 35 calculates blood pressure information by correcting the reference blood pressure information using the phase parameter θ serving as the correction value calculated by the phase parameter calculation unit 34. Specifically, the average blood pressure calculation unit 35 calculates the average blood pressure $P_{Ave}$ serving as the blood pressure information using the following equation (4)

[Math. 4]

$$p_{Ave} = p_{0Ave}\left\{1 + \tan^{-1}\left(\frac{\theta - \theta_0}{360}\right)\right\} \quad (4)$$

so that the initial average blood pressure $p_{0Ave}$ is corrected using a value of the phase parameter θ based on the initial phase parameter $\theta_0$. The calculated blood pressure information is transmitted to the computer 20 and displayed on the display unit of the computer 20. Specifically, when the initial average blood pressure $p_{0Ave}$=100 mmHg, the initial phase parameter $\theta_0$=300, and the phase parameter θ=327.93 calculated by the phase parameter calculation unit 34, the average blood pressure $p_{Ave}$ is calculated by the following equation:

[Math. 5]

$$p_{Ave} = 100\left\{1 + \tan^{-1}\left(\frac{327.93 - 300}{360}\right)\right\} = 108.$$

Figure 6:
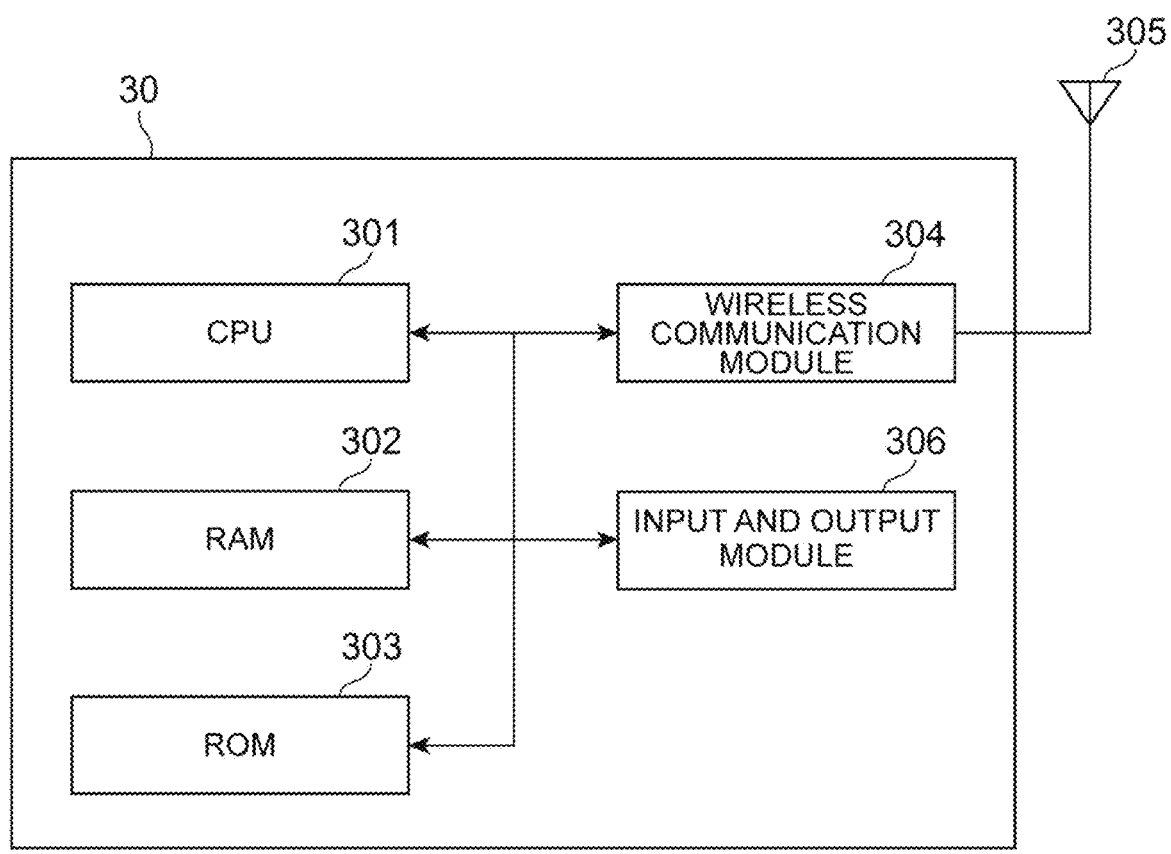
FIG. 6 is a diagram illustrating a hardware configuration of the processing unit in FIG. 1.

Next, a hardware configuration of the processing unit 30 will be described with reference to FIG. 6. FIG. 6 shows a hardware configuration of the processing unit 30 in FIG. 1. As illustrated in FIG. 6, the processing unit 30 is physically a computer including, for example, a central processing unit (CPU) 301 that is a processor, a random access memory (RAM) 302 or a read only memory (ROM) 303 that is a recording medium, a wireless communication module 304, an antenna 305, and an input and output module 306, which are electrically connected to each other. Each function of the processing unit 30 described above is realized by operating the wireless communication module 304, the antenna 305, and the input and output module 306 under the control of the CPU 301 by loading the blood pressure information calculating program or the like on hardware such as the CPU 301 and the RAM 302, and by performing reading and writing of data in the RAM 302. It should be noted that the processing unit 30 may include, for example, a display or an operation module.

Figure 7:
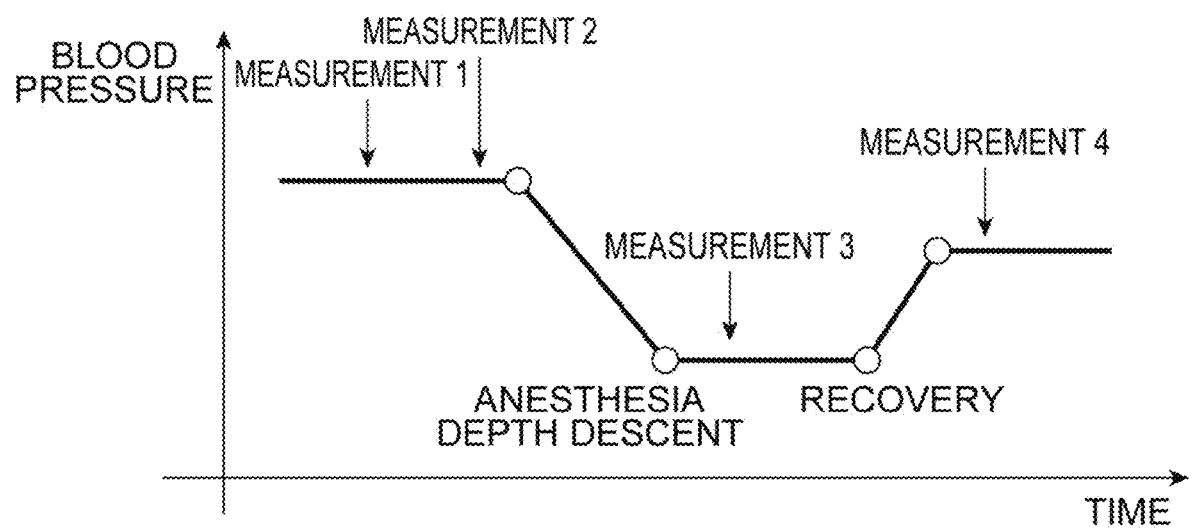
FIG. 7 is a graph illustrating variation in blood pressure of a cynomolgus monkey due to an anesthetic agent.

The present inventors have confirmed that the value of the blood pressure information calculated using Equation (4) above is statistically significant through the following experiment. The inventors of the present invention have continuously measured a blood pressure waveform indicating variation in blood pressure of a cynomolgus monkey while administering an isoflurane anesthetic agent having different concentrations to the cynomolgus monkey to vary the blood pressure in a state in which an invasive sphygmomanometer is installed in an artery of a foot of the cynomolgus monkey. FIG. 7 shows the variation in the blood pressure of the cynomolgus monkey due to the anesthetic agent. A horizontal axis of FIG. 7 indicates time and a vertical axis of FIG. 7 shows the blood pressure.

Figure 8:
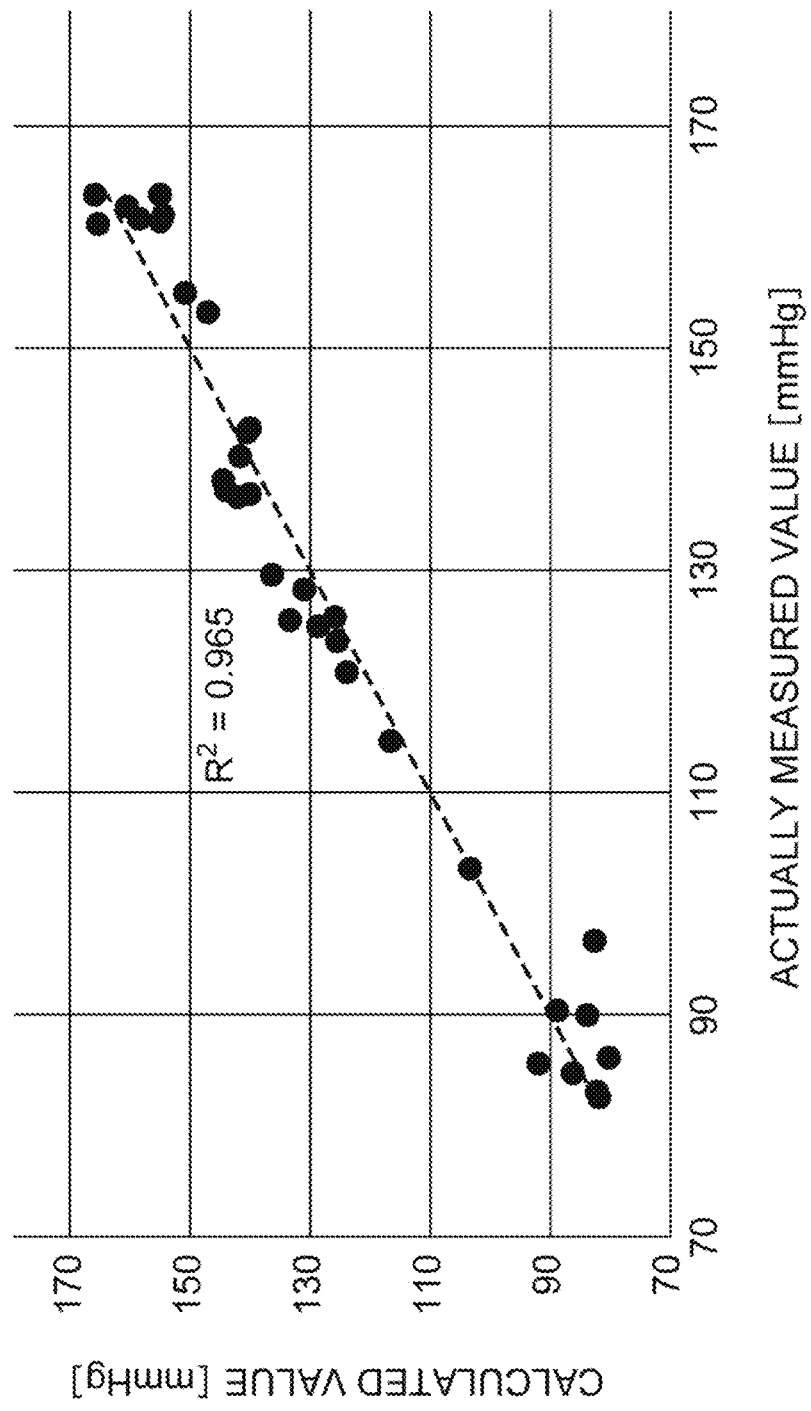
FIG. 8 is a graph illustrating a correlation between an average blood pressure value obtained through actual measurement and a calculated value of an average blood pressure based on a spectrum of a relative blood pressure waveform.

A plurality of pieces of data in different time periods in the measured blood pressure waveform were extracted, a relationship between an actually measured value of the average blood pressure obtained from the extracted data and a calculated value obtained using Equation (4) above on the basis of a spectrum obtained by performing Fourier transformation on the relative blood pressure waveform was plotted as shown in a graph of FIG. 8, and a correlation between these values was confirmed. A horizontal axis of FIG. 8 indicates an average blood pressure obtained through the experiment performed on the cynomolgus monkey, and a vertical axis of FIG. 8 indicates an average blood pressure based on the spectrum obtained by performing the Fourier transformation on the relative blood pressure waveform. It was confirmed that, as illustrated in FIG. 8, a correlation value between the average blood pressure obtained by performing the Fourier transformation on the relative blood pressure waveform and the average blood pressure obtained through the experiment performed on the cynomolgus monkey was in a range of R=0.965.

From the above, it was shown that the blood pressure information calculated by Equation (4) above was obtained with high accuracy.

Figure 9:
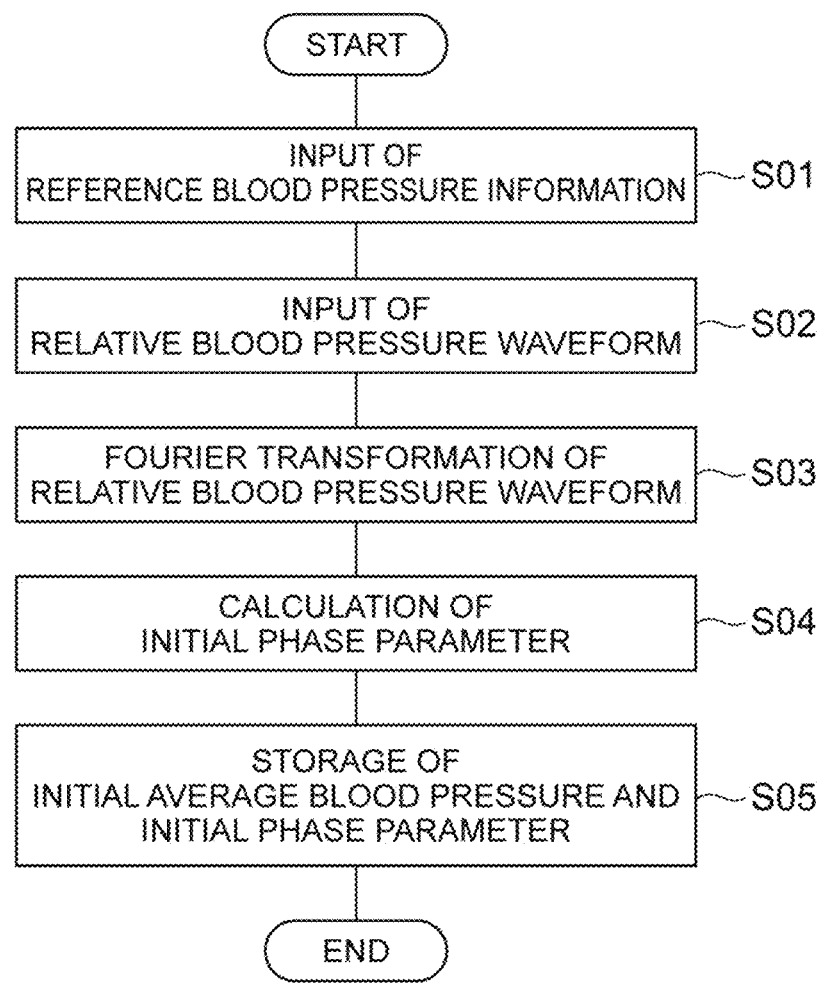
FIG. 9 is a flowchart illustrating a process of presetting reference blood pressure information in the blood pressure information calculation system 1 of FIG. 1.

Next, a procedure of a process of calculating the blood pressure information in the blood pressure information calculation system 1 including the blood pressure information calculating device 10 according to the embodiment will be described with reference to the flowcharts of FIGS. 9 to 10. FIG. 9 is a flowchart illustrating a process of presetting the reference blood pressure information in the blood pressure information calculation system 1, and FIG. 10 is a flowchart illustrating a blood pressure information calculation process in the blood pressure information calculation system 1.

It should be noted that the reference blood pressure information that is reference information for calculation of the blood pressure information is preset as a prerequisite for this process. As illustrated in FIG. 9, first, the reference blood pressure information from the computer 20 is input by the input unit 32, and the initial average blood pressure $p_{0Ave}$ is acquired on the basis of the reference blood pressure information (step S01: acquisition step). At the same time, the relative blood pressure waveform p' from the detection unit 11 is input by the input unit 32 (step S02). Subsequently, Fourier transformation is performed on the relative blood pressure waveform p' input in step S02 by the frequency domain representation conversion unit 33 to calculate an intensity spectrum and a phase spectrum (step S03). Subsequently, the calculation of Equation (3) is executed by the phase parameter calculation unit 34 using the intensity spectrum and the phase spectrum calculated in step S03 to calculate the initial phase parameter $\theta_0$ (step S04). Finally, the initial average blood pressure $p_{0Ave}$ acquired by the input unit 32 and the initial phase parameter $\theta_0$ calculated by the phase parameter calculation unit 34 are stored in the processing unit 30 in association with each other (step S05).

Figure 10:
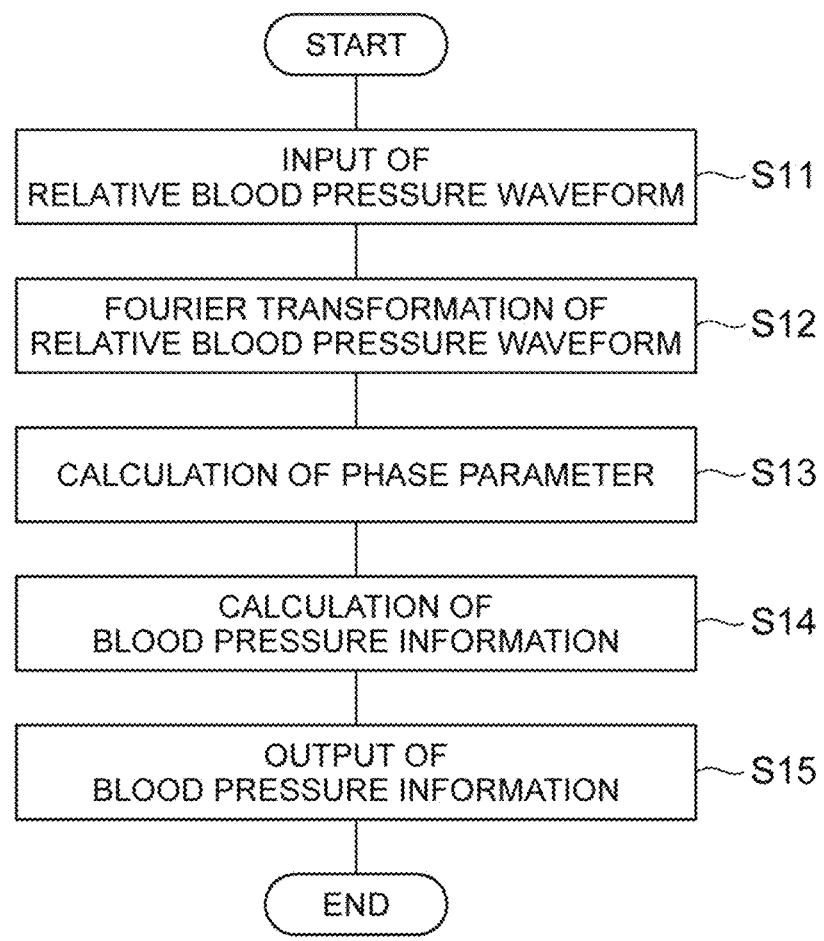
FIG. 10 is a flowchart illustrating a blood pressure information calculation process in the blood pressure information calculation system 1 of FIG. 1.

Thereafter, as illustrated in FIG. 10, when the blood pressure information calculation process is started, the relative blood pressure waveform p' from the detection unit 11 is input by the input unit 32 (step S11; acquisition step). Subsequently, Fourier transformation is performed on the relative blood pressure waveform p' input in step S11 by the frequency domain representation conversion unit 33 to calculate the intensity spectrum and the phase spectrum (step S12; spectrum calculation step). Subsequently, the calculation of the Equation (3) is executed by the phase parameter calculation unit 34 using the intensity spectrum and the phase spectrum calculated in step S12, to calculate the phase parameter $\theta$ (step S13; correction value calculation step). Then, the calculation of the Equation (4) using the combination of the pre-stored initial average blood pressure $p_{0Ave}$ and the pre-stored initial phase parameter $\theta_0$ and the phase parameter $\theta$ calculated in step S13 is executed by the average blood pressure calculation unit 35, to thereby calculate the average blood pressure $p_{Ave}$ serving as the blood pressure information (step S14; blood pressure information calculation step). Finally, the blood pressure information including the average blood pressure $p_{Ave}$ calculated in step S14 is output to the computer 20 (step S15). It should be noted that the same preset values may be repeatedly used for the initial average blood pressure $p_{0Ave}$ and the initial phase parameter $\theta_0$ used in step S14. The phase parameter $\theta$ calculated in step S13 and the average blood pressure $p_{Ave}$ calculated in step S15 may be used as the reference blood pressure information for the next calculation of the blood pressure information.

Figure 11:
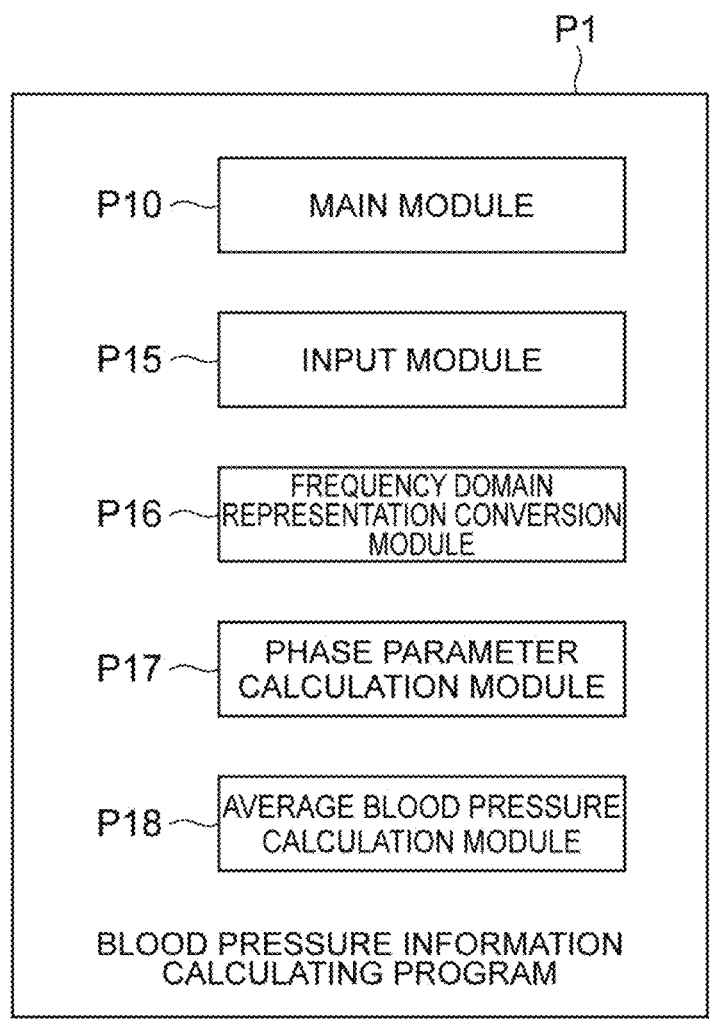
FIG. 11 is a diagram illustrating a configuration of a blood pressure information calculating program according to an embodiment of the present invention.

Next, a blood pressure information calculating program for causing a computer to function as the blood pressure information calculating device 10 will be described with reference to FIG. 11.

The blood pressure information calculating program P1 includes a main module P10, an input module P15, a frequency domain representation conversion module P16, a phase parameter calculation module P17, and an average blood pressure calculation module P18.

The main module P10 is a portion that controls the entire blood pressure information calculation process. Functions realized by executing the input module P15, the frequency domain representation conversion module P16, the phase parameter calculation module P17, and the average blood pressure calculation module P18 are the same as those of the input unit 32, the frequency domain representation conversion unit 33, the phase parameter calculation unit 34, and the average blood pressure calculation unit 35 of the blood pressure information calculating device 10, respectively.

The blood pressure information calculating program P1 is provided by, for example, a recording medium such as a CD-ROM, a DVD, or a ROM, or a semiconductor memory. In addition, the blood pressure information calculating program P1 may be provided over a network as a computer data signal superimposed on a carrier wave.

According to the blood pressure information calculating device 10, the blood pressure information calculating method, the blood pressure information calculating program P1, and the recording medium for recording the program according to the above-described embodiment, the phase parameter $\theta$ as the correction value is calculated using one of a phase of the frequency component (the main wave) corresponding to the pulse and a phase of a frequency component (second harmonic wave) that is twice that of the main wave on the basis of the phase spectrum calculated by performing Fourier transformation on the waveform based on the relative blood pressure waveform, and the average blood pressure $p_{Ave}$ is calculated by correcting the initial average blood pressure $p_{0Ave}$ serving as the reference blood pressure information using the correction value. The phase of the main wave or the phase of the second harmonic wave calculated in this way is highly correlated with the average blood pressure which is blood pressure information. Therefore, the average blood pressure $p_{Ave}$ obtained by correcting the reference blood pressure information using the correction value calculated from the phase has high accuracy. Therefore, it is possible to maintain the accuracy of the calculation of the average blood pressure regarding the absolute blood pressure waveform without repeating complicated operations, such as an operation of measuring the absolute blood pressure waveform using the sphygmomanometer or calculation of a resultant absolute blood pressure waveform.

Further, in the above-described embodiment, since the phase parameter θ that is the correction value is calculated through a product of the phase and the intensity, it is possible to further enhance accuracy of the average blood pressure $p_{Ave}$ obtained by correcting the initial average blood pressure $p_{0Ave}$.

Further, in the above embodiment, since the phase parameter θ that is the correction value is calculated using at least the sum of the product of the phase and the intensity of the main wave and the product of the phase and the intensity of the second harmonic wave, it is possible to further enhance the accuracy of the blood pressure information obtained by correcting the reference blood pressure information.

Furthermore, since the detection unit 11 is included in the above embodiment, it is possible to obtain the relative blood pressure waveform non-invasively and acquire the blood pressure information using the relative blood pressure waveform. Furthermore, since the sphygmomanometer 12 is further included in the above embodiment, it is possible to easily acquire and input the value that is a reference for calculation of the blood pressure information.

Second Embodiment

Next, an overview of the blood pressure information calculation system including the blood pressure information calculating device according to a second embodiment will be described. A difference between the blood pressure information calculation system according to the second embodiment and the blood pressure information calculation system according to the first embodiment is that an absolute blood pressure waveform is calculated as blood pressure information. The absolute blood pressure waveform is obtained by performing a transformation process on the relative blood pressure waveform on the basis of the average blood pressure obtained as in the first embodiment described above and a ratio of a maximum blood pressure to a minimum blood pressure obtained from the relative blood pressure waveform.

Figure 12:
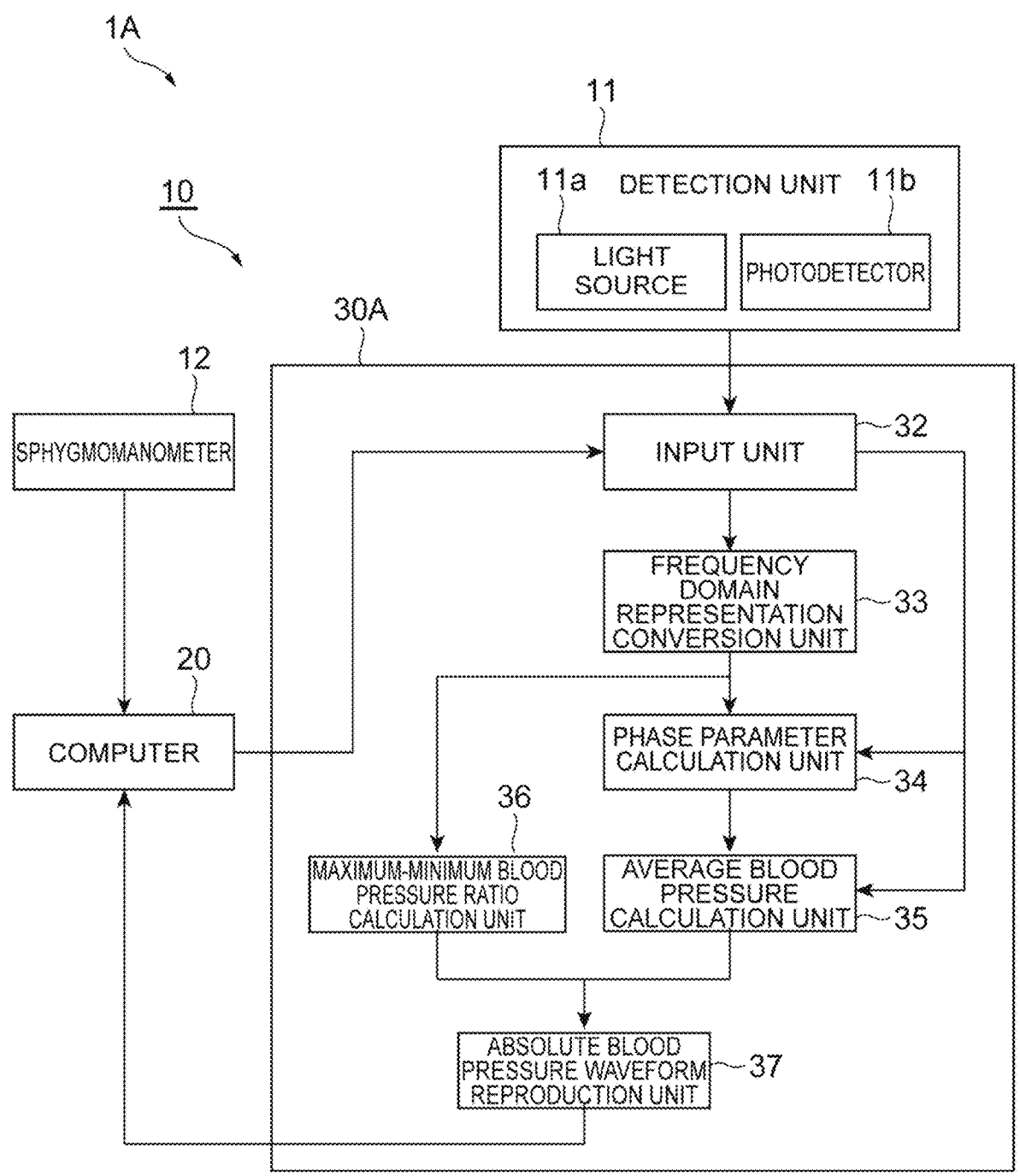
FIG. 12 is a functional block diagram of a blood pressure information calculation system according to a second embodiment of the present invention.

FIG. 12 is a functional block diagram of the blood pressure information calculation system according to the second embodiment. A difference between the blood pressure information calculation system 1A of according to the second embodiment which is illustrated in FIG. 12 and the blood pressure information calculation system 1 according to the first embodiment is that the function of the processing unit 30A is partially different from the function of the processing unit 30A.

That is, in the processing unit 30A according to the second embodiment, a maximum-minimum blood pressure ratio calculation unit 36 and an absolute blood pressure waveform reproduction unit 37 are included in addition to the input unit 32, the frequency domain representation conversion unit 33, the phase parameter calculation unit 34, and the average blood pressure calculation unit 35 having the same functions as those of the processing unit 30. However, the input unit 32 receives the volume pulse wave from the detection unit 11 and corrects the input volume pulse wave using the viscoelastic characteristics correction value indicating the viscoelastic characteristics of the blood vessel described above to acquire the relative blood pressure waveform p' on which an influence thereof has been reduced. The input unit 32 outputs the acquired relative blood pressure waveform p' to the frequency domain representation conversion unit 33 and the phase parameter calculation unit 34. Using the relative blood pressure waveform calculated by correcting the volume pulse wave with the viscoelastic characteristics correction value in this way, a degree of approximation to the actual blood pressure waveform of the absolute blood pressure waveform calculated by the processing unit 30 can be increased as compared with a case in which the volume pulse wave strongly influenced by the viscoelastic characteristics of the blood vessel is used as it is as the relative blood pressure waveform.

The maximum-minimum blood pressure ratio calculation unit 36 of the processing unit 30A calculates a maximum-minimum blood pressure ratio $P_{Tmin}:P_{Tmax}$ which is a ratio of the maximum blood pressure $P_{Tmax}$ to the minimum blood pressure $P_{Tmin}$ of the subject on the basis of the intensity spectrum P(f) equal to or higher than the frequency of the main wave in the intensity spectrum P(f) of the relative blood pressure waveform calculated by the frequency domain representation conversion unit 33. Specifically, the maximum-minimum blood pressure ratio calculation unit 36 calculates the maximum-minimum blood pressure ratio $P_{Tmin}:P_{Tmax}$ on the basis of Equation (5) below:

[Math. 6]

$$P_{Tmin}:P_{Tmax} = |P(f_1)| : \sum_{n=1}^{N} |P(f_n)|. \tag{5}$$

The maximum-minimum blood pressure ratio $P_{Tmin}:P_{Tmax}$ calculated in this way is a ratio of the peak value of the spectral intensity of the main wave in the intensity spectrum P(f) to a sum of peak values of the spectral intensity of waves higher than the main wave in the intensity spectrum P(f). The maximum-minimum blood pressure ratio calculation unit 36 outputs the calculated maximum-minimum blood pressure ratio $P_{Tmin}:P_{Tmax}$ to the absolute blood pressure waveform reproduction unit 37.

The absolute blood pressure waveform reproduction unit 37 calculates an absolute blood pressure waveform on the basis of the maximum-minimum blood pressure ratio $P_{Tmin}:P_{Tmax}$ calculated by the maximum-minimum blood pressure ratio calculation unit 36 and the average blood pressure $p_{Ave}$ calculated by the average blood pressure calculation unit 35. Here, the relative blood pressure waveform p' has values different from those of the absolute blood pressure waveform, but has a shape similar to the shape of the absolute blood pressure waveform. The relative blood pressure waveform p' has a lowest point corresponding to the minimum blood pressure value $P_{Tmin}$ that is a diastolic blood pressure in the absolute blood pressure waveform and a highest point corresponding to the maximum blood pressure value $P_{Tmax}$ that is a systolic blood pressure in the absolute blood pressure waveform. The lowest point in the relative blood pressure waveform p' is detected as, for example, a point at which the waveform intensity is a minimum in the relative blood pressure waveform p', and the highest point in the relative blood pressure waveform p' is detected as, for example, a point at which the waveform intensity is a maximum in the relative blood pressure waveform p'.

First, the absolute blood pressure waveform reproduction unit 37 corrects a scaling factor for the relative blood pressure waveform p' output from the input unit 32 on the basis of the maximum-minimum blood pressure ratio $P_{Tmin}:P_{Tmax}$ calculated by the maximum-minimum blood pressure ratio calculation unit 36. Specifically, the absolute blood pressure waveform reproduction unit 37 detects the lowest point and the highest point in the relative blood pressure waveform p' and calculates a ratio between the lowest point and the highest point that have been detected. Further, the absolute blood pressure waveform reproduction unit 37 adds an addition coefficient to the relative blood pressure waveform p' or multiplies the relative blood pressure waveform p' by a multiplication coefficient to correct the scaling factor in the relative blood pressure waveform p' so that the ratio is substantially equal to the maximum-minimum blood pressure ratio $P_{Tmin}:P_{Tmax}$. Thus, a scaling factor corrected relative blood pressure waveform is calculated.

Then, the absolute blood pressure waveform reproduction unit 37 corrects the value in the scaling factor corrected relative blood pressure waveform obtained by performing the scaling factor correction as described above, using the value of the average blood pressure $p_{Ave}$ and calculates the absolute blood pressure waveform. Specifically, the absolute blood pressure waveform reproduction unit 37 calculates the average value in the scaling factor corrected relative blood pressure waveform using Equation (1) above, Equation (2) above, or the like. Further, the absolute blood pressure waveform reproduction unit 37 adds an addition coefficient to the scaling factor corrected relative blood pressure waveform or multiplies the scaling factor corrected relative blood pressure waveform by a multiplication coefficient to correct the relative blood pressure waveform so that the calculated average value is substantially equal to the average blood pressure $p_{Ave}$. The absolute blood pressure waveform reproduction unit 37 outputs the calculated absolute blood pressure waveform p to the computer 20.

Figure 13:
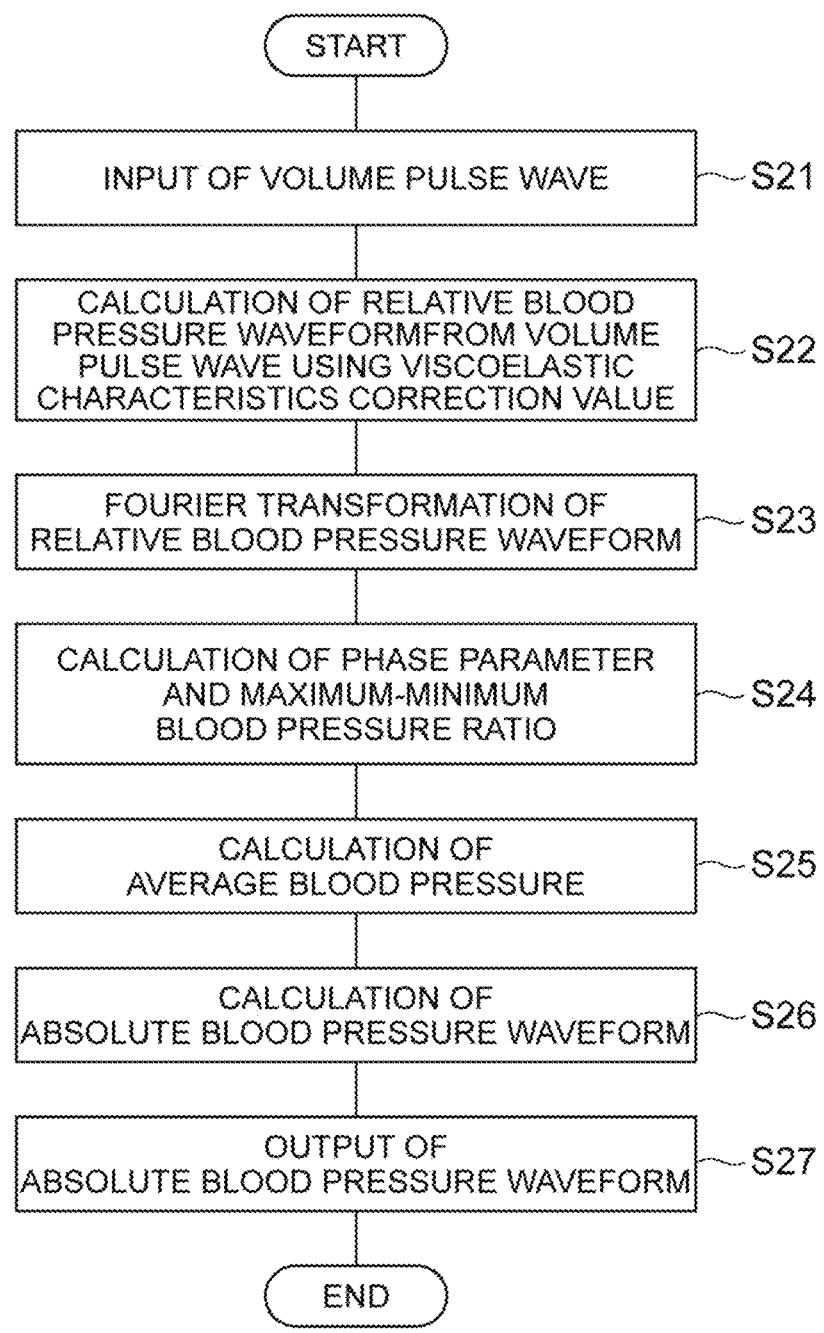
FIG. 13 is a flowchart illustrating a procedure of a process of calculating blood pressure information in the blood pressure information calculation system of FIG. 12.

FIG. 13 is a flowchart illustrating a procedure of a blood pressure information calculation process in the blood pressure information calculation system 1A according to the embodiment. As illustrated in FIG. 13, when a process of calculating the blood pressure information is started, the volume pulse wave from the detection unit 11 is input by the input unit 32 (step S21; acquisition step). Then, the input volume pulse wave is corrected using the viscoelastic characteristics correction value indicating the viscoelastic characteristics of the blood vessel by the input unit 32, and the relative blood pressure waveform p' is calculated (step S22). Subsequently, Fourier transformation is performed on the relative blood pressure waveform p' corrected in step S22 by the frequency domain representation conversion unit 33, and the intensity spectrum and the phase spectrum are calculated (step S23; spectrum calculation step). Subsequently, the phase parameter θ is calculated by the phase parameter calculation unit 34 using the intensity spectrum and the phase spectrum calculated in step S23. At the same time, the maximum-minimum blood pressure ratio $P_{Tmin}:P_{Tmax}$ is calculated by the maximum-minimum blood pressure ratio calculation unit 36 using the intensity spectrum (step S24; correction value calculation step). Then, the average blood pressure $p_{Ave}$ is calculated by the average blood pressure calculation unit 35 using a combination of the initial average blood pressure $p_{0Ave}$ and the initial phase parameter $θ_0$ stored in advance and the phase parameter θ calculated in step S24 (step S25; blood pressure information calculation step). The absolute blood pressure waveform p is calculated by the absolute blood pressure waveform reproduction unit 37 from the relative blood pressure waveform p' on the basis of the maximum-minimum blood pressure ratio $P_{Tmin}:P_{Tmax}$ and the average blood pressure $p_{Ave}$ (step S26; blood pressure waveform calculation step). Finally, the blood pressure information including the absolute blood pressure waveform p calculated in step S26 is output to the computer 20 (step S27).

Further, the blood pressure information calculating program for causing the computer to function as the processing unit 30A according to the embodiment is the same as the blood pressure information calculating program P1 according to the first embodiment, includes a main module P10, an input module P15, a frequency domain representation conversion module P16, a phase parameter calculation module P17, and an average blood pressure calculation module P18, and further includes a maximum-minimum blood pressure ratio calculation module and an absolute blood pressure waveform reproduction module. Functions realized by executing the maximum-minimum blood pressure ratio calculation module and the absolute blood pressure waveform reproduction module are the same as the functions of the maximum-minimum blood pressure ratio calculation unit 36 and the absolute blood pressure waveform reproduction unit 37, respectively.

In the second embodiment described above, it is possible to continuously obtain a highly accurate absolute blood pressure waveform without repeating a complicated operation such as a measurement operation for an absolute blood pressure waveform using a sphygmomanometer.

Although various embodiments of the present invention have been described above, the present invention is not limited to the above-described embodiments, and the present invention may be modified within the scope without changing the gist described in each claim or may be applied to others.

For example, in the blood pressure information calculation system 1 or 1A according to the above embodiment, the configuration excluding the computer 20 is the blood pressure information calculating device 10, but the present invention is not limited thereto. For example, in the blood pressure information calculation system 1 or 1A, the configuration including the computer 20 in addition to the blood pressure information calculating device 10 may be the blood pressure information calculating device. Instead of the blood pressure information calculating device 10, the computer 20 may be the blood pressure information calculating device. In a case in which the computer 20 is the blood pressure information calculating device, the computer 20 has the each function of the processing unit 30 or 30A described above. Further, for example, in the blood pressure information calculation system 1 or 1A, the computer 20 and the processing unit 30 or 30A may be integrally configured.

Figure 14:
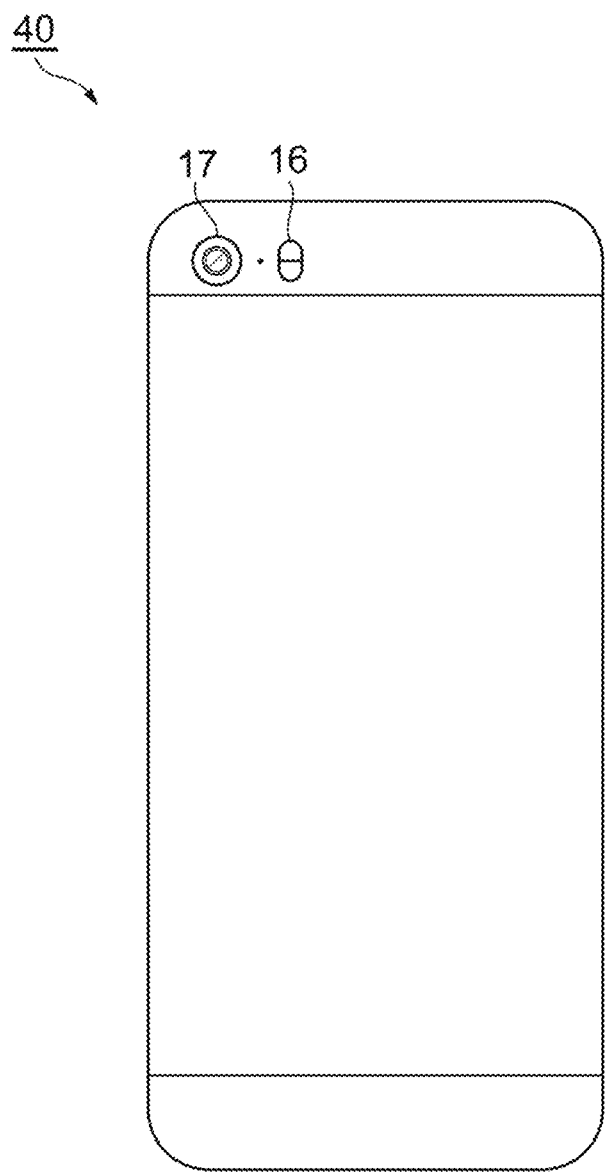
FIG. 14 is a schematic configuration diagram illustrating a blood pressure information calculating device according to a modification example.

Further, for example, as illustrated in FIG. 14, the blood pressure information calculating device may be configured as a communication terminal 40 such as a smartphone. The communication terminal such as a smartphone is a kind of a computer including a processor, a storage medium, and the like. In this case, the communication terminal 40 has, for example, the same function as each function of the blood pressure information calculating device 10 or the computer 20 described above as functions of the blood pressure information calculating device. Further, the communication terminal 40 may have each function of the computer 20 in addition to each function of the blood pressure information calculating device 10 or may have each function of the computer 20 in addition to each function of the blood pressure information calculating device 10. That is, each function of the blood pressure information calculating device 10 and each function of the computer 20 according to the above embodiment may be realized in an integrated configuration.

It should be noted that the communication terminal 40 includes a flash lamp 16 as a light source, and a camera 17 as a photodetector. The flash lamp 16 and the camera 17 are, for example, functions originally included in the communication terminal 40. In this modification example, the light from the flash lamp 16 is radiated from the surface of the living body toward the inside thereof in a state in which the surface (for example, a finger) of the living body that is a subject is placed on both the flash lamp 16 and the camera 17. Light from the living body is detected by the camera 17 and acquired as the volume pulse wave or the relative blood pressure waveform. Thus, the functions originally included in the communication terminal 40 can also serve as a function of the acquisition unit that acquires the volume pulse wave or the relative blood pressure waveform. Further, the communication terminal 40 may include a light source and a photodetector for acquiring the volume pulse wave or the relative blood pressure waveform, in addition to the flash lamp 16 and the camera 17. Further, a processor such as a tablet computer, a computer including a processor and a storage medium, or the like may be used instead of the communication terminal 40.

Further, for example, as illustrated in FIG. 15, a blood pressure information calculating device 10C in which the detection unit 11 and the processing unit 30 are integrated may be used as the blood pressure information calculating device. The blood pressure information calculating device 10C is attached to the surface of the living body H, and integrally includes, for example, a communication unit 14, a processing unit 30, a power supply unit 15, and a detection unit 11 including a light source 11a and a photodetector 11b.

Further, the phase parameter calculation unit 34 of the above embodiment may calculate the phase parameter θ using Equation (6) below or Equation (7) below, in addition to Equation (3) above.

[Math. 7]
$$\theta = \sum_{n=1}^{N} \frac{|P(f_n)|}{|P_0(f_n)|} \frac{1}{n} (\arg(P(f_n)) - \arg(P_0(f_n))) \quad (6)$$

[Math. 8]
$$\theta = \int_{f_1}^{f_N} |P(x)| \arg(P(x)) dx. \quad (7)$$

In Equation (6) above, $P_0(f)$ is an intensity spectrum obtained by performing the Fourier transformation on the relative blood pressure waveform p' or the absolute blood pressure waveform p in correspondence to the time of the acquisition of the reference blood pressure information, and $\arg(P_0(f))$ is a phase spectrum obtained by performing the Fourier transformation on the relative blood pressure waveform p' or the absolute blood pressure waveform p in correspondence to the time of the acquisition of the reference blood pressure information. Since the phase parameter calculated using such an equation also has a high correlation with the blood pressure information of the subject, the accuracy of the blood pressure information calculated on the basis of this phase parameter is also high.

Further, when the phase parameter calculation unit 34 of the above embodiment calculates the phase parameter θ, the phase parameter calculation unit 34 may calculate the phase values $\arg(P(f_1))$ and $\arg(P(f_2))$ corresponding to the frequency of the main wave or the second harmonic wave of the phase spectrum themselves to be equal to the phase parameter θ. Further, the phase parameter θ may be obtained as at least a sum of the phase values $\arg(P(f_1))$ and $\arg(P(f_2))$ of the main wave and the second harmonic wave. Further, the phase value $\arg(P(f_1))$ of the main wave (or the second harmonic wave) multiplied by the intensity value $P(f_1)$ of the main wave (or the second harmonic wave) may be equally set to the phase parameter θ.

Further, when the initial average blood pressure $P_{0Ave}$ is calculated in the above embodiment, the initial average blood pressure $P_{0Ave}$ may be calculated using Equation (2) above on the basis of the maximum blood pressure and the minimum blood pressure obtained from the sphygmomanometer 12 and the relative blood pressure waveform obtained from the detection unit 11 at the same time.

In addition, the surface of the living body that is the subject may be a portion other than a palm or a finger, and may be a forehead, an upper arm, a neck, an earlobe, or the like.

Here, in the blood pressure information calculating device according to the above embodiment, the spectrum calculation unit may further calculate the intensity spectrum of the waveform based on the pulse wave, and the correction value calculation unit may calculate the correction value by further using at least one of the intensity of the main wave and the intensity of the second harmonic wave in the intensity spectrum. Further, in the blood pressure information calculating method according to the above embodiment, in the spectrum calculation step, the intensity spectrum of the waveform based on the pulse wave may be further calculated, and in the correction value calculation step, the correction value may be calculated by further using at least one of the intensity of the main wave and the intensity of the second harmonic wave in the intensity spectrum. When such a configuration is adopted, it is possible to further improve the accuracy of the blood pressure information obtained by correcting the reference blood pressure information.

Furthermore, in the blood pressure information calculating device according to the above embodiment, the correction value calculation unit may set the frequency of the main wave or the frequency of the second harmonic wave according to the peak of the intensity spectrum. Furthermore, in the blood pressure information calculating method according to the above embodiment, in the correction value calculation step, the frequency of the main wave or the frequency of the second harmonic wave may be set according to the peak of the intensity spectrum. Thus, it is possible to further enhance the accuracy of the blood pressure information obtained by correcting the reference blood pressure information.

Furthermore, in the blood pressure information calculating device according to the above embodiment, the correction value calculation unit may calculate the correction value through a product of the phase and the intensity. Furthermore, in the blood pressure information calculating method according to the above embodiment, in the correction value calculation step, the correction value may be calculated through the product of the phase and the intensity. In this case, it is possible to further enhance the accuracy of the blood pressure information obtained by correcting the reference blood pressure information.

Furthermore, in the blood pressure information calculating device according to the embodiment, the correction value calculation unit may calculate the correction value using at least the sum of the value based on the phase of the main wave and the value based on the phase of the second harmonic wave. Furthermore, in the blood pressure information calculating method according to the above embodiment, in the correction value calculation step, the correction value may be calculated using at least the sum of the value based on the phase of the main wave and the value based on the phase of the second harmonic wave. In this case, it is possible to further enhance the accuracy of the blood pressure information obtained by correcting the reference blood pressure information.

Further, in the blood pressure information calculating device according to the above embodiment, the blood pressure information may include an average blood pressure of the inspection target. Further, in the blood pressure information calculating method according to the above embodiment, the blood pressure information may include the average blood pressure of the inspection target.

Furthermore, the blood pressure information calculating device according to the above embodiment may further include a blood pressure waveform calculation unit for calculating an absolute blood pressure waveform of the inspection target on the basis of the waveform based on the pulse wave and the blood pressure information. Furthermore, the blood pressure information calculating method according to the above embodiment may further include a blood pressure waveform calculation step of calculating the absolute blood pressure waveform of the inspection target on the basis of the waveform based on the pulse wave and the blood pressure information. When such a configuration is adopted, it is possible to continuously obtain a highly accurate absolute blood pressure waveform without repeating complicated operations such as a measurement operation using a sphygmomanometer.

Furthermore, the blood pressure information calculating device according to the above embodiment may further include a light source for irradiating the inspection target with light, and a photodetector for detecting light from the inspection target and inputting a detection signal to the input unit as a waveform based on a pulse wave. In this case, it is possible to obtain a waveform based on the pulse wave non-invasively and acquire the blood pressure information using the waveform.

Furthermore, the blood pressure information calculating device according to the above embodiment may further include a sphygmomanometer for detecting the blood pressure of the inspection target and inputting reference blood pressure information based on a detection result to the input unit. By adopting such a configuration, it is possible to easily acquire and input a value serving as a reference for calculation of the blood pressure information.

INDUSTRIAL APPLICABILITY

One embodiment of the present invention is applied to a blood pressure information calculating device, a blood pressure information calculating method, a blood pressure information calculating program, and a recording medium for recording the program, and enables the accuracy of calculation of a value regarding the blood pressure waveform to be maintained without requiring a complicated operation.

REFERENCE SIGNS LIST 1, 1A Blood pressure information calculation system
10, 10C Blood pressure information calculating device
11 Detection unit
11a Light source
11b Photodetector
12 Sphygmomanometer
30, 30A Processing unit
32 Input unit
33 Frequency domain representation conversion unit (spectrum calculation unit)
34 Phase parameter calculation unit (correction value calculation unit)
35 Average blood pressure calculation unit (blood pressure information calculation unit)
37 Absolute blood pressure waveform reproduction unit (blood pressure waveform calculation unit)
40 Communication terminal
H Living body
P1 Blood pressure information calculating program

The invention claimed is:

1. A device for calculating blood pressure information regarding a blood pressure value of an inspection target, the device comprising:
   a processor configured to input a waveform based on a pulse wave of the inspection target and reference blood pressure information serving as a reference for calculating the blood pressure information on the basis of the waveform based on the pulse wave, the blood pressure information being one or more of a systolic blood pressure, a diastolic blood pressure, and an average blood pressure;
   perform, by the processor, Fourier transformation on the waveform based on the pulse wave and calculate a phase spectrum of a waveform based on the pulse wave,
   calculate, by the processor, an intensity spectrum of the waveform based on the pulse wave,
   calculate, by the processor, a correction value using at least one of a phase of a main wave which is a frequency corresponding to a pulse of the inspection target and a phase of a second harmonic wave corresponding to a second harmonic wave of the main wave on the basis of the phase spectrum and using at least one of an intensity of the main wave and an intensity of the second harmonic wave in the intensity spectrum, wherein the correction value is calculated using a product of the phase and the intensity, and
   calculate, by the processor, the blood pressure information by correcting the reference blood pressure information using the correction value.

2. The device according to claim 1, wherein processor sets a frequency of the main wave or a frequency of the second harmonic wave according to a peak of the intensity spectrum.

3. The device according to claim 1, wherein processor calculates the correction value by at least using a sum of a value based on the phase of the main wave and a value based on the phase of the second harmonic wave.

4. The device according to claim 1, wherein the blood pressure information includes an average blood pressure of the inspection target.

5. The device according to claim 1, wherein the processor calculates an absolute blood pressure waveform of the inspection target on the basis of the waveform based on the pulse wave and the blood pressure information.

6. The device according to claim 1, further comprising:
a light source configured to irradiate the inspection target with light; and
a photodetector configured to detect light from the inspection target and input a detection signal to the processor as a waveform based on the pulse wave.

7. The device according to claim 1, further comprising:
a sphygmomanometer configured to detect blood pressure of the inspection target and input the reference blood pressure information based on a detection result to the processor.

8. A method of calculating blood pressure information regarding a blood pressure value of an inspection target, the method comprising:
acquiring a waveform based on a pulse wave of the inspection target and reference blood pressure information serving as a reference for calculating the blood pressure information on the basis of the waveform based on the pulse wave, the blood pressure information being one or more of a systolic blood pressure, a diastolic blood pressure, and an average blood pressure;
performing Fourier transformation on the waveform based on the pulse wave and calculating a phase spectrum of a waveform based on the pulse wave;
calculating an intensity spectrum of the waveform based on the pulse wave;
calculating a correction value using at least one of a phase of a main wave which is a frequency corresponding to a pulse of the inspection target and a phase of a second harmonic wave corresponding to a second harmonic wave of the main wave on the basis of the phase spectrum and using at least one of an intensity of the main wave and an intensity of the second harmonic wave in the intensity spectrum, wherein the correction value is calculated using a product of the phase and the intensity; and
calculating the blood pressure information by correcting the reference blood pressure information using the correction value.

9. The method according to claim 8, wherein calculating of the correction value includes setting a frequency of the main wave or a frequency of the second harmonic wave according to a peak of the intensity spectrum.

10. The method according to claim 8, wherein calculating of the correction value includes calculating the correction value by at least using a sum of a value based on the phase of the main wave and a value based on the phase of the second harmonic wave.

11. The method according to claim 8, wherein the blood pressure information includes an average blood pressure of the inspection target.

12. The method according to claim 8, further comprising:
calculating an absolute blood pressure waveform of the inspection target on the basis of the waveform based on the pulse wave and the blood pressure information.

13. A non-transitory computer-readable recording medium having a program for causing a computer to execute a process of calculating blood pressure information regarding a blood pressure value of an inspection target, the program causing the computer to function as:
inputting a waveform based on a pulse wave of the inspection target and reference blood pressure information serving as a reference for calculating the blood pressure information on the basis of the waveform based on the pulse wave, the blood pressure information being one or more of a systolic blood pressure, a diastolic blood pressure, and an average blood pressure;
performing Fourier transformation on the waveform based on the pulse wave and calculating a phase spectrum of a waveform based on the pulse wave;
calculating an intensity spectrum of the waveform based on the pulse wave;
calculating a correction value using at least one of a phase of a main wave which is a frequency corresponding to a pulse of the inspection target and a phase of a second harmonic wave corresponding to a second harmonic wave of the main wave on the basis of the phase spectrum and using at least one of an intensity of the main wave and an intensity of the second harmonic wave in the intensity spectrum, wherein the correction value is calculated using a product of the phase and the intensity; and
calculating the blood pressure information by correcting the reference blood pressure information using the correction value.

14. A device for calculating blood pressure information regarding a blood pressure value of an inspection target, the device comprising:
a processor configured to input a waveform based on a pulse wave of the inspection target and reference blood pressure information serving as a reference for calculating the blood pressure information on the basis of the waveform based on the pulse wave, the blood pressure information being one or more of a systolic blood pressure, a diastolic blood pressure, and an average blood pressure;
perform, by the processor, Fourier transformation on the waveform based on the pulse wave and calculate a phase spectrum of a waveform based on the pulse wave,
calculate, by the processor, a correction value by at least using a sum of a value based on a phase of a main wave which is a frequency corresponding to a pulse of the inspection target and a value based on a phase of a second harmonic wave corresponding to a second harmonic wave of the main wave on the basis of the phase spectrum, and
calculate, by the processor, the blood pressure information by correcting the reference blood pressure information using the correction value.

15. A method of calculating blood pressure information regarding a blood pressure value of an inspection target, the method comprising:
acquiring a waveform based on a pulse wave of the inspection target and reference blood pressure information serving as a reference for calculating the blood pressure information on the basis of the waveform based on the pulse wave, the blood pressure information being one or more of a systolic blood pressure, a diastolic blood pressure, and an average blood pressure;
performing Fourier transformation on the waveform based on the pulse wave and calculating a phase spectrum of a waveform based on the pulse wave;
calculating a correction value by at least using a sum of a value based on a phase of a main wave which is a frequency corresponding to a pulse of the inspection target and a value based on a phase of a second harmonic wave corresponding to a second harmonic wave of the main wave on the basis of the phase spectrum, and calculating the blood pressure information by correcting the reference blood pressure information using the correction value.

16. A non-transitory computer-readable recording medium having a program for causing a computer to execute a process of calculating blood pressure information regarding a blood pressure value of an inspection target, the program causing the computer to function as:

inputting a waveform based on a pulse wave of the inspection target and reference blood pressure information serving as a reference for calculating the blood pressure information on the basis of the waveform based on the pulse wave, the blood pressure information being one or more of a systolic blood pressure, a diastolic blood pressure, and an average blood pressure;

performing Fourier transformation on the waveform based on the pulse wave and calculating a phase spectrum of a waveform based on the pulse wave;

calculating a correction value by at least using a sum of a value based on a phase of a main wave which is a frequency corresponding to a pulse of the inspection target and a value based on a phase of a second harmonic wave corresponding to a second harmonic wave of the main wave on the basis of the phase spectrum, and calculating the blood pressure information by correcting the reference blood pressure information using the correction value.

* * * * *